(12) United States Patent
Robbins et al.

(10) Patent No.: US 8,530,429 B2
(45) Date of Patent: Sep. 10, 2013

(54) BRAIN TUMOR TARGETING PEPTIDES AND METHODS

(75) Inventors: Stephen Mark Robbins, Calgary (CA); Jennifer Rahn, Calgary (CA); Donna Lorraine Senger, Calgary (CA)

(73) Assignee: Arch Cancer Therapeutics, Inc., Calgary (CA)

( * ) Notice: Subject to any disclaimer, the term of this patent is extended or adjusted under 35 U.S.C. 154(b) by 372 days.

(21) Appl. No.: 12/950,855

(22) Filed: Nov. 19, 2010

(65) Prior Publication Data

US 2011/0129418 A1   Jun. 2, 2011

Related U.S. Application Data

(60) Provisional application No. 61/264,064, filed on Nov. 24, 2009.

(51) Int. Cl.
*A61P 35/00* (2006.01)
*C07K 7/00* (2006.01)

(52) U.S. Cl.
USPC ............................ 514/19.3; 530/327; 530/326

(58) Field of Classification Search
USPC .................................. 514/19.3; 530/327, 326
See application file for complete search history.

(56) References Cited

FOREIGN PATENT DOCUMENTS

| WO | WO 2009/015843 A1 | 2/2009 |
|---|---|---|
| WO | WO 2009021137 A2 | 2/2009 |

OTHER PUBLICATIONS

Regina et al. (Brit. J. Pharmacol. 2008, 155: 185-197).*
Nagy et al. (Curr. Pharm. Des. 2005, 11 (9): 1167-80).*
Kondo et al., "Potent synergy of dual antitumor peptides for growth suppression of human glioblastoma cell lines", Mol. Cancer Therapeut., vol. 7, No, 6, pp. 1461-1471 (2008).
Oka et al., "Brain tumor stem cells from an adenoid glioblastoma multiforme", Neurol Med Chir. (Tokyo), vol. 49, pp. 146-151 (2009).
Reardon et al, "Cilengitide: An integrin-targeting arginine-glycine-aspartic acid peptide with promising activity for glioblastoma multiforme", Exp. Opin. Investig. Drugs, vol. 17, No. 8, pp. 1225-1235 (20O0).
Regina et al., "Antitumour activity of ANG1005, a conjugate between paclitaxel and the new brain delivery vector angiopep-2", Brit. J. Pharmacol,, vol. 155, pp. 185-197 (2008).
Zhang et al., "Neuroblastoma tumor cell-binding peptides identified through random peptide phage display", vol. 171, No. 2, pp. 153-164 (2001).

* cited by examiner

*Primary Examiner* — Stephen Rawlings
*Assistant Examiner* — Yan Xiao
(74) *Attorney, Agent, or Firm* — King & Spalding LLP; Peter J. Dehlinger

(57) ABSTRACT

A method of diagnosing and treating a human glioblastoma multiforme (GBM) brain tumor in a subject is disclosed. The method includes administering to the subject, an effective amount of composition having a peptide 12-20 amino acid residues in length and selected for its ability to bind preferentially to a subtype of human GBM cells identified as brain tumor initiating cells (BTICs) or highly invasive glioma cells (HIGCs). Also disclosed are a phage-display screening method for identifying such therapeutic peptides, and peptides that hind specifically to BTICs or HIGCs.

6 Claims, 11 Drawing Sheets

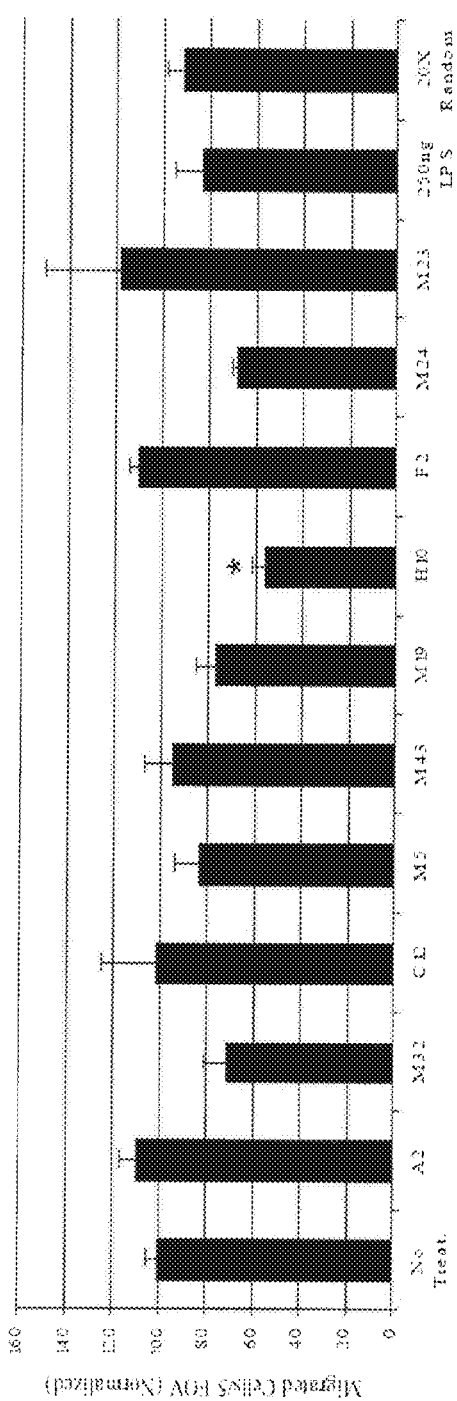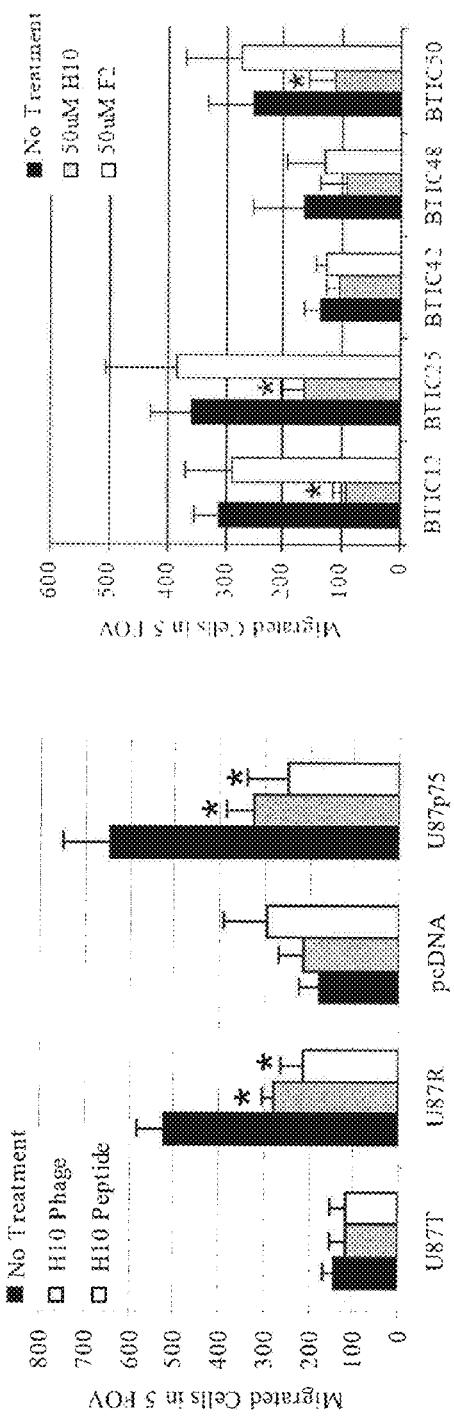

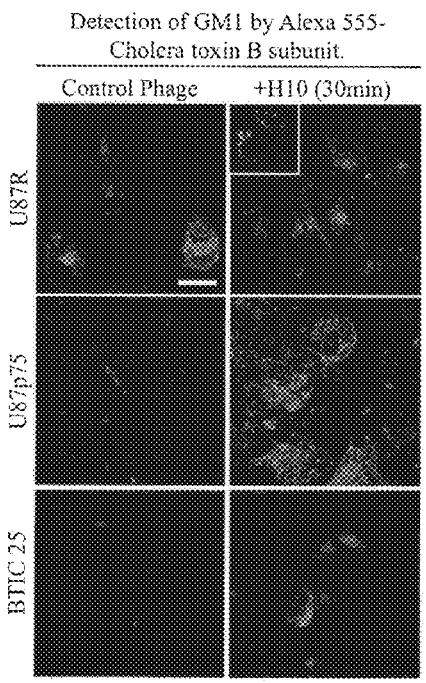
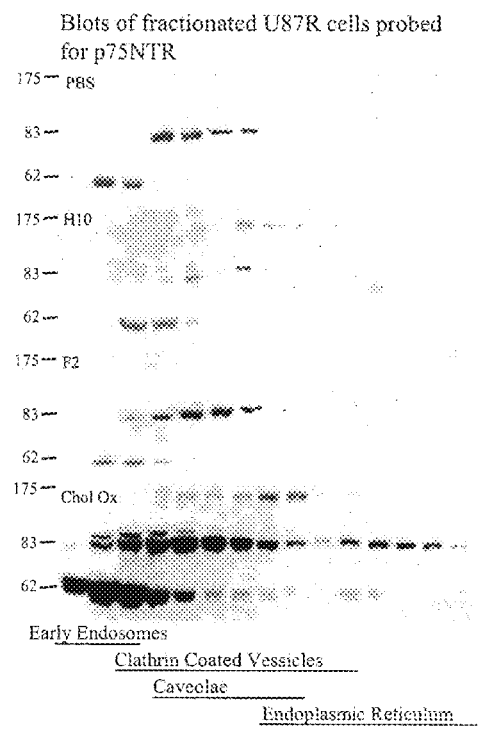
Fig. 4A
Fig. 4B
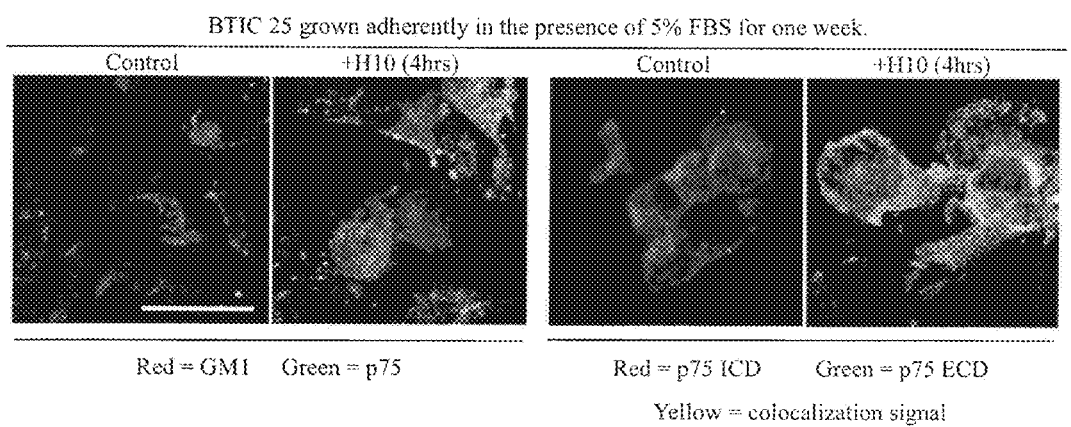
Fig. 4C

| | Main Location | U87MG (Parental) | NSC | BTIC12 | BTIC25 | BTIC42 | BTIC48 | BTIC50 |
|---|---|---|---|---|---|---|---|---|
| 7A | throughout | - | -20% | ++40% | +50% | -5% | - | ++5% |
| 10C | throughout | +40% | - | ++5% | - | -50% | +50% | -90% |
| E10 | granular or throughout | -+95% | - | -+90% | +85% | -+60 | -+90% | -95% |
| 3F | membrane | -10% | - | - | - | - | +25% | -95% |
| C1 | throughout | ++60% | +++95% | -+90% | +++95% | +++95% | +20% | ++95% |
| 3B | membrane | ++10% | ++80% | -+50% | ++70% | -95% | +-70% | ++90% |

SEQUENCE LISTING

```
<160> NUMBER OF SEQ ID NOS: 18

<210> SEQ ID NO 1
<211> LENGTH: 12
<212> TYPE: PRT
<213> ORGANISM: Artificial Sequence
<220> FEATURE:
<223> OTHER INFORMATION: synthetic HIGC targeting peptide

<400> SEQUENCE: 1

Ser Val Ser Val Gly Met Lys Pro Ser Pro Arg Pro
1               5                   10

<210> SEQ ID NO 2
<211> LENGTH: 12
<212> TYPE: PRT
<213> ORGANISM: Artificial Sequence
<220> FEATURE:
<223> OTHER INFORMATION: synthetic HIGC targeting peptide

<400> SEQUENCE: 2

Gly Ile Ser Leu Ser Ser Tyr Leu Gln Ser Thr Gln
1               5                   10

<210> SEQ ID NO 3
<211> LENGTH: 12
<212> TYPE: PRT
<213> ORGANISM: Artificial Sequence
```

```
<220> FEATURE:
<223> OTHER INFORMATION: synthetic HIGC targeting peptide

<400> SEQUENCE: 3

Glu His Met Ala Leu Thr Tyr Pro Phe Arg Pro Pro
1               5                   10

<210> SEQ ID NO 4
<211> LENGTH: 12
<212> TYPE: PRT
<213> ORGANISM: Artificial Sequence
<220> FEATURE:
<223> OTHER INFORMATION: synthetic HIGC targeting peptide

<400> SEQUENCE: 4

His Trp Ala Pro Ser Met Tyr Asp Tyr Val Ser Trp
1               5                   10

<210> SEQ ID NO 5
<211> LENGTH: 12
<212> TYPE: PRT
<213> ORGANISM: Artificial Sequence
<220> FEATURE:
<223> OTHER INFORMATION: synthetic HIGC targeting peptide

<400> SEQUENCE: 5

Arg Thr Val Pro Asp Tyr Thr Ala His Val Arg Thr
1               5                   10

<210> SEQ ID NO 6
<211> LENGTH: 12
<212> TYPE: PRT
<213> ORGANISM: Artificial Sequence
<220> FEATURE:
<223> OTHER INFORMATION: synthetic HIGC targeting peptide

<400> SEQUENCE: 6

Ser Gly His Gln Leu Leu Leu Asn Lys Met Pro Asn
1               5                   10

<210> SEQ ID NO 7
<211> LENGTH: 12
<212> TYPE: PRT
<213> ORGANISM: Artificial Sequence
<220> FEATURE:
<223> OTHER INFORMATION: synthetic HIGC targeting peptide

<400> SEQUENCE: 7

Thr Asn Ser Ile Trp Tyr Thr Ala Pro Tyr Met Phe
1               5                   10

<210> SEQ ID NO 8
<211> LENGTH: 12
<212> TYPE: PRT
<213> ORGANISM: Artificial Sequence
<220> FEATURE:
<223> OTHER INFORMATION: synthetic HIGC targeting peptide

<400> SEQUENCE: 8

Gly Met Ser Leu Ser Arg Gln Met Leu Trp Ser Leu
1               5                   10

<210> SEQ ID NO 9
<211> LENGTH: 12
<212> TYPE: PRT
<213> ORGANISM: Artificial Sequence
<220> FEATURE:
<223> OTHER INFORMATION: synthetic HIGC targeting peptide
```

```
<400> SEQUENCE: 9

His Leu Phe Pro Gln Ser Asn Tyr Gly Gly His Ser
1               5                   10

<210> SEQ ID NO 10
<211> LENGTH: 12
<212> TYPE: PRT
<213> ORGANISM: Artificial Sequence
<220> FEATURE:
<223> OTHER INFORMATION: synthetic HIGC targeting peptide
<220> FEATURE:
<221> NAME/KEY: misc_feature
<222> LOCATION: (11)..(11)
<223> OTHER INFORMATION: Xaa can be any naturally occurring amino acid

<400> SEQUENCE: 10

Cys Ile Gln Leu Ala Asn Pro Pro Arg Leu Xaa Gly
1               5                   10

<210> SEQ ID NO 11
<211> LENGTH: 12
<212> TYPE: PRT
<213> ORGANISM: Artificial Sequence
<220> FEATURE:
<223> OTHER INFORMATION: synthetic BTIC targeting peptide

<400> SEQUENCE: 11

Pro Ser Pro His Arg Gln Arg Gln His Ile Leu Arg
1               5                   10

<210> SEQ ID NO 12
<211> LENGTH: 12
<212> TYPE: PRT
<213> ORGANISM: Artificial Sequence
<220> FEATURE:
<223> OTHER INFORMATION: synthetic BTIC targeting peptide

<400> SEQUENCE: 12

Gln Thr Ile Arg Ile Ile Ile Arg Arg Ser Arg Thr
1               5                   10

<210> SEQ ID NO 13
<211> LENGTH: 12
<212> TYPE: PRT
<213> ORGANISM: Artificial Sequence
<223> OTHER INFORMATION: synthetic BTIC targeting peptide

<400> SEQUENCE: 13

Ser Leu His Met Arg His Lys Arg Lys Pro Arg Arg
1               5                   10

<210> SEQ ID NO 14
<211> LENGTH: 12
<212> TYPE: PRT
<213> ORGANISM: Artificial Sequence
<220> FEATURE:
<223> OTHER INFORMATION: synthetic BTIC targeting peptide

<400> SEQUENCE: 14

Ser Ser Arg Ser Met Gln Arg Thr Leu Ile Ile Ser
1               5                   10

<210> SEQ ID NO 15
<211> LENGTH: 12
<212> TYPE: PRT
<213> ORGANISM: Artificial Sequence
```

```
<220> FEATURE:
<223> OTHER INFORMATION: synthetic BTIC targeting peptide

<400> SEQUENCE: 15

Ile Arg Ser Ile Arg Met Arg Arg Ile Leu Ile Leu
1               5                   10

<210> SEQ ID NO 16
<211> LENGTH: 12
<212> TYPE: PRT
<213> ORGANISM: Artificial Sequence
<220> FEATURE:
<223> OTHER INFORMATION: synthetic BTIC targeting peptide

<400> SEQUENCE: 16

Lys Thr Ser Met Arg Pro Leu Ile Leu Ile His Ile
1               5                   10

<210> SEQ ID NO 17
<211> LENGTH: 19
<212> TYPE: PRT
<213> ORGANISM: Artificial Sequence
<220> FEATURE:
<223> OTHER INFORMATION: synthetic carrier peptide

<400> SEQUENCE: 17

Thr Phe Phe Tyr Gly Gly Ser Arg Gly Lys Arg Asn Asn Phe Lys Thr
1               5                   10                  15

Glu Glu Tyr

<210> SEQ ID NO 18
<211> LENGTH: 19
<212> TYPE: PRT
<213> ORGANISM: Artificial Sequence
<220> FEATURE:
<223> OTHER INFORMATION: synthetic carrier peptide

<400> SEQUENCE: 18

Thr Phe Phe Tyr Gly Gly Ser Arg Gly Arg Arg Asn Asn Phe Arg Thr
1               5                   10                  15

Glu Glu Tyr
```

BRAIN TUMOR TARGETING PEPTIDES AND METHODS

CROSS-REFERENCE TO RELATED APPLICATIONS

This application claims the benefit of U.S. Provisional Application No. 61/264,064, filed Nov. 24, 2009, which is incorporated herein by reference in its entirety.

FIELD OF THE INVENTION

The present invention relates to the field of peptides capable of targeting malignant glioma cells, and in particular, a brain tumor initiating cell (BTIC) subtype of human glioblastoma multiforme (GBM) cells and highly invasive glioma cell (HIGC) subtype of human GBM cells, and to methods employing the peptides.

REFERENCES

1. Van Meir, E. G., Hadjipanayis, C. G., Norden, A. D., Shu, H. K., Wen, P. Y., and Olson, J. J. Exciting new advances in neuro-oncology: the avenue to a cure for malignant glioma. CA Cancer J Clin 60, 166-193.

2. Train, B., and Rosenthal, M. A. Survival comparison between glioblastoma multiforme and other incurable cancers. J Clin Neurosci 17, 417-421.

3. Lacroix, M., Abi-Said, D., Foumey, D. R., Gokaslan, Z. L., Shi, W., DeMonte, F., Lang, F. F., McCutcheon, I. E., Hassenbusch, S. J., Holland, E., Hess, K., Michael, C., Miller, D., and Sawaya, R. (2001). A multivariate analysis of 416 patients with glioblastoma multiforme: prognosis, extent of resection, and survival. J Neurosurg 95, 190-198.

4. Mangiola, A., de Bonis, P., Maira, G., Balducci, M., Sica, G., Lama, G., Lauriola, L., and Anile, C. (2008). Invasive tumor cells and prognosis in a selected population of patients with glioblastoma multiforme. Cancer 113, 841-846.

5. Wang, L., Rahn, J. J., Lun, X., Sun, B., Kelly, J. J., Weiss, S., Robbins, S. M., Forsyth, P. A., and Senger, D. L. (2008). Gamma-secretase represents a therapeutic target for the treatment of invasive glioma mediated by the p75 neurotrophin receptor. PLoS Biol e289.

6. Johnston, A. L., Lun, X., Rahn, J. J., Liacini, A., Wang, L., Hamilton, M. G., Parney, I. F., Hempstead, B. L., Robbins, S. M., Forsyth, P. A., and Senger, D. L. (2007). The p75 neurotrophin receptor is a central regulator of glioma invasion, PLoS Biol 5, e212.

7. Koukourakis, G. V., Kouloulias, V., Zacharias, G., Papadimitriou, C., Pantelakos, P., Maravelis, G., Fotineas, A., Beli, I., Chaideopoulos, D., and Kouvaris, J. (2009). Temozolornide with radiation therapy in high grade brain gliomas: pharmaceuticals considerations and efficacy; a review article. Molecules 14, 1.561-1577.

8. Kitange, G. J., Carlson, B. L., Schroeder, M. A., Grogan, P. T., Lamont, J. D., Decker, P. A., Wu, W., James, C. D., and Sarkaria, J. N. (2009). Induction of MGMT expression is associated with temozolomide resistance in glioblastoma xenografts. Neuro Oncol 11, 281-291.

9. Halatsch, M. E., Low, S., Mursch, K., Hielscher, T., Schmidt, U., Unterberg, A., Vougioukas, V. I., and Feuerhake, F. (2009). Candidate genes for sensitivity and resistance of human glioblastoma multiforme cell lines to erlotinib. Laboratory investigation. J Neurosurg 111, 211-218.

10. Mukherjee, B., McEllin, B., Camacho, C. V., Tornimatsu, N., Sirasanagandala, S., Nannepaga, S., Hatanpaa, K. J., Mickey, B., Madden, C., Maher, E., Boothman, D. A., Furnari, F., Cavenee, W. K., Bachoo, R. M., and Burma, S. (2009). EGFRvIII and DNA double-strand break repair: a molecular mechanism for radioresistance in glioblastoma. Cancer Res 69, 4252-4259.

11. Reya, T., Morrison, S. J., Clarke, M. F., and Weissman, I. L. (2001). Stem cells, cancer, and cancer stem cells. Nature 414, 105-111.

12. Bonnet, D., and Dick, J. E. (1997). Human acute myeloid leukemia is organized as a hierarchy that originates from a primitive hernatopoietic cell. Nat Med 3, 730-737.

13. Lagasse, E., and Weissman, I. L. (1997). Enforced expression of Bcl-2 in monocytes rescues macrophages and partially reverses osteopetrosis in op/op mice. Cell 89, 1021-1031.

14. Traver, D., Akashi, K., Weissman, I. L., and Lagasse, E. (1998), Mice defective in two apoptosis pathways in the myeloid lineage develop acute myeloblastic leukemia. Immunity 9, 47-57.

15. Nowell, P. C., and Croce, C. M. (1986). Chromosomes, genes, and cancer. Am J Pathol 125, 7-15.

16. Sidransky, D., Mikkelsen, T., Schwechheimer, K., Rosenblum, M. L., Cavanee, W., and Vogelstein, B. (1992). Clonal expansion of p53 mutant cells is associated with brain tumour progression. Nature 355, 846-847.

17, Shackleton, M., Valliant, F., Simpson, K. J., Stingl, J., Smyth, G. K., Asselin-Labat, M. L., Wu, L., Lindeman, G. J., and Visvader, J. E. (2006). Generation of a functional mammary gland from a single stern cell. Nature 439, 84-88.

18. Clarke, M. F., Dick, J. E., Dirks, P. B., Eaves, C. J., Jamieson, C. H., Jones, Visvader, J., Weissman, I. L., and Wahl, G. M. (2006). Cancer stem cells-perspectives on current status and future directions: AACR Workshop on cancer stein cells. Cancer Res 66, 9339-9344, 19. Hemmati, H. D., Nakano, I., Lazareff, J. A., Masterman-Srnith, M., Geschwind, Bronner-Fraser, M., and Komblum, H. I. (2003). Cancerous stem cells can arise from pediatric brain tumors. Proc Natl Acad Sci USA 100, 15178-15183.

20. Singh, S. K., Clarke, I. D., Terasaki, M., Bonn, V. E., Hawkins, C., Squire, J., and Dirks, P. B. (2003). Identification of a cancer stem cell in human brain tumors. Cancer Res 63, 5821-5828.

21. Singh, S. K., Clarke, I. D., Hide, T., and Dirks, P. B. (2004). Cancer stem cells in nervous system tumors. Oncogene 23, 7267-7273.

22. Bao, S., Wu, Q., McLendon, R. E., Hao, Y., Shi, Q., Hjelnieland, A. B., Dewhirst, Bigner, D. D., and Rich, J. N. (2006). Glioma stem cells promote radioresistance by preferential activation of the DNA damage response. Nature 444, 756-760.

23. Lee, J., Kotliarova, S., Kotliarov, Y., Li, A., Su, Q., Donin, N. M., Pastorino, S., Purow, B. W., Christopher, N., Mang, W., Park, J. K., and Fine, H. A. (2006). Tumor stein cells derived from glioblastomas cultured in bFGF and EGF more closely mirror the phenotype and genotype of primary tumors than do serum-cultured cell lines. Cancer Cell 9, 391-403.

24. Piccirillo, S. G., Combi, R., Cajola, L., Patrizi, A., Redaelli, S., Bentivegna, A., Baronchelli, S., Maira, G., Polio, B., Mangiola, A., DiMeco, F., Dalpra, L., and Vescovi, A. L. (2009). Distinct pools of cancer stem-like cells coexist within human glioblastomas and display different tumorigenicity and independent genomic evolution. Oncogene 28, 1807-1811.

25. Vescovi, A. L., Galli, R., and Reynolds, B. A. (2006). Brain tumour stem cells. Nat Rev Cancer 6, 425-436.

26. Wu, Y., and Wu, P. Y. (2009). CD133 as a marker for cancer stem cells: progresses and concerns. Stem Cells Dev 18, 1127-1134.

27. Cheng, J. X., Liu, B. L., and Zhang, X. (2009). How powerful is CD133 as a cancer stem cell marker in brain tumors? Cancer Treat Rev 35, 403-408.

28. Kelly, J. J., Stechishin, O., Chojnacki, A., Lun, X., Sun, B., Senger, D. L., Forsyth, P., Auer, R. N., Dunn, J. F., Cairncross, J. G., Purley, I. F. and Weiss, S. (2009). Proliferation of human glioblastoma stem cells occurs independently of exogenous mitogens. Stem Cells 27, 1722-1733.

29. Reynolds, B. A., and Weiss, S. (1992). Generation of neurons and astrocytes from isolated cells of the adult mammalian central nervous system. Science 255, 1707-1710.

30. Oh, Y., Mohiuddin, I., Sun, Y., Putnam, J. B., Jr., Hong, W. K., Arap, and Pasqualini, R. (2005). Phenotypic diversity of the lung vasculature in experimental models of metastases. Chest 128, 596S-600S.

31. Rafii, S., Avecilla, S. T., and Jin, D. K. (2003). Tumor vasculature address book: identification of stage-specific tumor vessel zip codes by phage display, Cancer Cell 4, 331-333.

32. Hart, S. L., Knight, A. M., Harbottle, R. P., Mistry, A., Hunger, H. D., Cutler, D. F., Williamson, R., and Coutelle, C. (1994), Cell binding and internalization by filamentous phage displaying a cyclic Arg-Gly-Asp-containing peptide. J Biol Chem 269, 12468-12474.

33. Koivunen, E., Wang, B., and Ruoslahti, E. (1994). Isolation of a highly specific ligand for the alpha 5 beta 1 integrin from a phage display library. J Cell Biol 124, 373-380.

34. Koivunen, E., Gay, D. A., and Ruoslahti, E. (1993), Selection of peptides binding to the alpha 5 beta 1 integrin from phage display library. J Biol Chem 268, 20205-20210.

35. Arap, W., Pasqualini, R., and Ruoslahti, E. (1998). Cancer treatment by targeted drug delivery to tumor vasculature in a mouse model. Science 279, 377-380.

36. Norris, J. D., Paige, L. A., Christensen, D. J., Chang, C. Y., Huacani, M. R., Fan, D., Hamilton, P. T., Fowlkes, D. M., and McDonnell, D. P. (1999). Peptide antagonists of the human estrogen receptor. Science 285, 744-746.

37. Mang, J., Spring, H., and Schwab, M. (2001). Neuroblastoma tumor cell-binding peptides identified through random peptide phage display. Cancer Lett 171, 153-164.

38. Rasmussen, U. B., Schreiber, V., Schultz, H., Misehier, F., and Sehughart, K. (2002). Tumor cell-targeting by phage-displayed peptides. Cancer Gene Ther 9, 606-612.

39. Auriac, A., Willemetz, A., and Canorme-Hergaux, F. Lipid rafts-dependent endocytosis: a new route for hepcidin-mediated regulation of ferroportin in macrophages. Haematologica.

40. Lindner, R., and Knorr, R. (2009). Rafting trips into the cell. Commun Integr Biol 2, 420-421.

41. Patra, S. K. (2008). Dissecting lipid raft facilitated cell signaling pathways in cancer. Biochim Biophys Acta 1785, 182-206.

42. Rollason, R., Korolchuk, V., Hamilton, C., Schu, P., and Banting, G. (2007). Clathrin-mediated endocytosis of a lipid-raft-associated protein is mediated through a dual tyrosine motif. J Cell Sci 120, 3850-3858.

43. Ostrom, R. S., and Liu, X. (2007). Detergent and detergent-free methods to define lipid rafts and caveolae. Methods Mol Biol 400, 459-468.

44. Echarri, A., Muriel, O., and Del Pozo, M. A. (2007). Intracellular trafficking of rafticaveolae domains: insights from integrin signaling. Semin Cell Dev Biol 627-637.

45. Gimpl, G., and Gehrig-Burger, K. (2007). Cholesterol reporter molecules. Biosci Rep 27, 335-358.

46. Rouquette-Jazdanian, A. K., Pelassy, C., Breittmayer, J. P., and Aussel, C. (2006). Revaluation of the role of cholesterol in stabilizing rafts implicated in T cell receptor signaling. Cell Signal 18, 105-1.22.

47. Pang, H., Le, P. U., and Nabi, I. R. (2004). Ganglioside GM1 levels are a determinant of the extent of caveolae/raft-dependent endocytosis of cholera toxin to the Golgi apparatus. J Cell Sci 117, 1421-1430.

48. Singh, R. D., Puri, V., Valiyaveettil, J. T., Marks, D. L., Bittman, R., and Pagano, R. E. (2003). Selective caveolin-1-dependent endocytosis of glycosphingolipids. Mol Biol Cell 14, 3254-3265.

49. Gil, C., Cubi, R., and Aguilera, J. (2007). Shedding of the p75NTR neurotrophin receptor is modulated by lipid rafts. FIBS Lett 581, 1851-1858.

50. Ezratty, E. J., Bertaux, C., Marcantonio, E. E., and Gundersen, G. G. (2009), Clathrin mediates integrin endocytosis for focal adhesion disassembly in migrating cells. J Cell Biol 187, 733-747.

51. di Blasio, L., Droetto, S., Norman, J., Bussolino, F., and Primo, L. Protein Kinase D1 Regulates VEGF-A-Enduced alphavbeta3 Integrin Trafficking and Endothelial Cell Migration. Traffic.

52. Miaczynska, M., and Bar-Sagi, D. Signaling endosomes: seeing is believing, Curr Opin Cell Biol, 53. Una, S., Escudero, C. A., Ramos, P., Lisbona, F., Allende, E., Covarrubias, P., Parraguez, J. I., Zampieri, N., Chao, M. V., Annaert, W., and Bronfman, F. C. (2007). TrkA receptor activation by nerve growth factor induces shedding of the p75 neurotrophin receptor followed by endosomal gamma-secretase-mediated release of the p75 intracellular domain. J Biol Chem 282, 7606-7615.

54. Jabbour, M. N., and Matioli, G. T. (2006). Age dependent and cello origin (stem versus progenitor) of a selected group of spontaneous brain tumors in humans. Med Hypotheses 67, 1437-1442.

55. Trog, D., Yeghiazaryan, K., Fountoulakis, M., Friedlein, A., Moenkemann, H., Haertel, N., Schueller, H., Breipohl, W., Schild, H., Leppert, D., and Golubnitschaja, O. (2006). Pro-invasive gene regulating effect of irradiation and combined temozolomide-radiation treatment on surviving human malignant glioma cells. Eur J Pharmacol 542, 8-15.

56. Trog, D., Yeghiazaryan, K., Schild, H. H., and Golubnitschaja, O. (2008). Engineering of clinical glioma treatment: prediction of pro-invasive molecular events in treated gliomas. Proc Inst Mech Eng H 222, 1149-1160.

57. Bronfman, F. C., Tcherpakov, M., Jovin, T. M., and Fainzilber, M. (2003). Ligand-induced internalization of the p75 neurotrophin receptor: a slow route to the signaling endosome. J Neurosci 23, 3209-3220.

58. Deinhardt, K., Reversi, A., Berninghausen, O., Hopkins, C. R., and Schiavo, G. (2007). Neurotrophins Redirect p75NTR from a clathrin-independent to a clathrin-dependent endocytic pathway coupled to axonal transport. Traffic 8, 1736-1749.

59. Bilderback, T. R., Gazula, V. R., Lisanti, M. P., and Dobrowsky, R. T. (1999). Caveolin interacts with Trk A and p75(NTR) and regulates neurotrophin signaling pathways. J Biol Chem 274, 257-263.

60. Bilderback, T. R., Grigsby, R. J., and Dobrowsky, R. T. (1997). Association of p75(NTR) with caveolin and localization of neurotrophin-induced sphingomyelin hydrolysis to caveolae. J Biol Chem 272, 10922-10927.

61. Barbass, C. B., D. R. Scott, J. K. Silverman, G. J. (2004). Phage Display: A Laboratory Manual, 1st Edition (Cold Spring Harbor Lab Press).

62. Drappatz J, Brenner A J, Rosenfeld S et al. ANG 1005: results of a Phase I study in patients with recurrent malignant glioma. J. Clin, Oncol. 28(15 Suppl.) (2010) (Abstract 2009).

63. Pardridge, W. M., Drug Delivery to the Brian, Journal of Cerebral Blood Flow & Metabolism (1997) 17, 713-731.

64. Gabathuler, R., CNS Neur0l Disord Drug Targets, 8(3): 195-204 (2009).

65. Menei P. et al., Expert Opin Drug Deliv, 2005 March; 2(2):363-76.

66. Stukel, J. et al., Expert Opin Drug Deliv, June, (2009).

67. Gelperina, S., et al., Eur. J. Pharma. And Bioptiarrna, 74(2): 157-163 (February 2010).

68. Gil, E S, et al., Biomacromolecules, 10(3):505-516, March, 2009).

69. Koziara, I. M., at el., J. Controlled Release, 99(2): 259-269 (September, 2004).

70. Yang, Z. et al., J Roy Soc Interface, 7(Supp4):S411-S422 (June, 2010).

71. Agarwal, A., et al., Curr. Pharm Des, 15(8):917-925 (2009).

BACKGROUND OF THE INVENTION

Glioblastoma multiforme (GBM) is a complex and heterogeneous disease, with prevalent short-term relapse and a median survival time of about 1 year when treated with surgery, radiotherapy and temozolomide [1-3]. Categorization by transcriptional clustering into proneural (better patient survival profile), indeterminant ("neural"), mesenchymal (associated with NF-1 loss) and proliferative ("classical"; associated with EGFR mutation or amplification) subtypes (reviewed in [1]) has underscored the usefulness of individualized patient profiles in determining prognosis as well as rational selection of targeted therapeutics, however a practical approach to targeting these subtypes clinically needs to be developed.

Despite intensive radio- and chemotherapy, tumor regrowth is virtually inevitable and typically occurs within a few centimeters of the resection margin [4]. There are two potential disease reservoirs that may contribute to treatment failure. First, invasive glioma has been characterized by recent clinical and in vitro studies which have shown that genetically and phenotypically distinct cells can form long tendrils which extend several centimeters away from the main tumor mass, or form diffusely spread, invasive subpopulations of tumor that are resistant to chemo- and radiotherapy, by virtue of their remote localization from the main tumor site [4-6], as well as expression of drug resistance genes and enhanced DNA repair capabilities [7-10]. These cells are referred to herein as highly invasive glioma cells, or FIIGC's.

The second putative reservoir is based on concept of Cancer Stem Cells (CSCs), which arose because mechanisms of self-renewal were similar between stem cells and cancer cells [11]. The cancer stem cell hypothesis proposes that a rare population of transformed stem cells, or progenitor cells with acquired self-renewal properties are the source of tumor cell renewal. Evidence for the existence of cancer stem cells has been suggested for a number of hematological malignancies [12-14] and more recently for a number of solid tumors [14-18].

There is now accumulating in vitro and in vivo data supporting the involvement of CSCs in glioblastoma [19-25]. The concept of brain tumor stem cells, or as they are referred to herein, as brain tumor-initiating cells or BTICs, is potentially important since they would define a tumor's behavior including proliferation, progression and response to therapy. One of the most important features of BTICs is that they closely resemble the human disease and therefore may be the best system for understanding brain tumor biology and developing therapeutics [23]. In addition, BTICs have fewer cytogenetic and molecular abnormalities [21, 23], which should make identifying causal events (i.e. instead of changes which occur as a consequence of transformation) in brain tumor formation easier. It should be clearly stated that the presence of a BTIC and the exact operational definition and use of terminology is a topic of great debate. As CD133 is controversial as an indicator of "stemness"[26-28], it is proposed herein that BTICs be defined as patient-derived cells with the ability to self-renew, differentiate into multiple lineages and form tumors in vivo 1281.

SUMMARY OF THE INVENTION

The invention includes, in one aspect, a peptide composition for targeting one of (i) a highly invasive glioma cell (HIGC) subtype of human glioblastoma multiforme (GBM) cells characterized by their ability to migrate from one brain hemisphere into which the cells are injected into the contralateral hemisphere, and (ii) a brain tumor initiating cell (BTIC) subtype of human GBM cells characterized by their stem-cell like properties of being able to self renew, generate spheres without the addition of exogenous mitogens and growth factors, and induce tumor formation in vivo when placed in the brains of immunocompromised mice. The composition includes an isolated peptide of between 12-20 amino acids and containing a sequence selected from the group consisting of SEQ ID NOS: 1-10, for targeting HIGCs, and SEQ ID NOS: 11-16, for targeting BTICs.

The peptide of the composition may be composed of L-amino acids, D-amino acids, a mixture of L- and D-amino acids, or a retro-inverso peptide formed of D-amino acids arranged in reverse order.

For use in localizing of HIGCs or BTICs in a subject with a human GBM tumor, the composition may include a radioimaging agent conjugated to the peptide.

For use in inhibiting or killing HIGCs or BTICs in a subject with a human GBM tumor, the composition may further include an anti-tumor agent conjugated to the peptide.

For use in targeting HIGCs, the peptide may contain a sequence selected from the group consisting of SEQ ID NOS: 1-10, preferably SEQ ID NOS: 2, 7, and 9, and more preferably, the sequence identified by SEQ ED NOS: 7.

For use in targeting BTICs, the peptide may contain a sequence selected from the group consisting of SEQ ID NOS: 11-16, preferably SEQ ID NOS: 11., 13, and 16, more preferably the sequence identified by SEQ ID NOS: 11.

For use in delivery to a patient human GBM tumor across the blood-brain barrier, the isolated peptide may be conjugated to a carrier peptide having the sequence identified by SEQ ID NOS: 17 or 18, and in another embodiment, may be encapsulated within a nanoparticle formed of poly(lactide-co-glycolide) copolymer, a cyclodextrin, or cetyl alcohol/polysorbate.

Also disclosed is the use of the above peptide composition for detecting the presence of HIGC or BTIC subtypes of cells in a patient with a human GBM tumor, where the composition includes a detectable radioimaging agent conjugated to the peptide. The peptide in an exemplary composition for detecting the presence of an HIGC subtype of cells contains the sequence SEQ ID NO: 7. The peptide in an exemplary composition for detecting the presence of a BTIC subtype class of cells contains the sequence SEQ ID NO: 11.

Further disclosed is the use of the above peptide composition, for inhibiting or killing HIGC or BTIC subtypes of cells in a patient with a human glioblastoma multiform (GBM) tumor, where the composition includes an anti-tumor agent conjugated to the peptide. The peptide in one exemplary composition for inhibiting or killing an HUE subtype of cells contains the sequence SEQ ID NO: 7. The peptide in an exemplary composition for inhibiting or killing a BTIC subtype of cells contains the sequence SEQ ID NO: 11.

In another aspect, the invention includes an improvement in a method for of treating a GBM tumor in a patient, by characterizing and/or treating subpopulations of tumor cells that represent the molecular heterogeneity of malignant glioma and are likely causes of tumor recurrence. The method includes administering to the patient, a peptide composition containing a peptide between 12-20 amino acids in length that has been selected for its preferential binding to one of (i) a highly invasive glioma cell (HIGC) subtype of human GBM cells characterized by their ability to migrate from one brain hemisphere into which the cells are injected into the contralateral hemisphere, and (ii) a brain tumor initiating cell (BTIC) subtype of human GB M cells characterized by their stem-cell like properties of being able to self renew, generate spheres without the addition of exogenous mitogens and growth factors, and induce tumor formation in vivo when placed in the brains of immunocompromised mice. Localization of the peptide composition at the targeted HIGC and/or BTIC subtypes of cells allows (i) the presence of cells of the targeted subtype to be detected, where the peptide composition includes a detectable radioimaging agent conjugated to the peptide, (ii) the targeted HGIC or BTIC cells to be inhibited or killed, where the peptide composition includes an anti-cancer agent conjugated to peptide, and (iii) migration of HGIC cells toward a tumor site to be inhibited by the peptide alone.

For use in characterizing subpopulations of tumor cells that are likely causes of tumor recurrence, the isolated peptide in the composition may include a peptide that contains one of the sequences SEQ ID NOS: 1-46 and has a radio-imaging agent conjugated thereto, and the method includes imaging the region of the tumor in the patient to detect localized radio-imaging agent.

For or use in inhibiting or killing subpopulations of tumor cells that are likely causes of tumor recurrence, the peptide in the peptide composition may contain one of the sequences SEQ ID NOS: 1-46 and has a anti-tumor agent conjugated thereto, and the peptide composition is administered in a therapeutically effective amount.

For use in inhibiting the migration of a highly invasive subpopulation of cells toward a tumor site, the peptide in the peptide composition may be simply a peptide having one of the sequences identified by SEQ ID NOS: 1-10.

The composition may be administered by one or more of: (i) intravenously, (ii) intra-arterially, (iii) administering the peptide by convection-enhanced diffusion (CED) an intra-ventricular-placed catheter; (iv) releasing the peptide from an intracerebral implant, (v) physically disrupting the blood brain barrier, (vi) intravenously or intra-arterially administering the peptide encapsulate u within nanoparticles, (vii) intravenously or intra-arterially administering the peptide conjugated to an Angio-pep carrier peptide, and (viii) administering the peptide intrathecally.

In still another aspect, the invention includes of identifying peptide compounds for the diagnosis or treatment of human GBM tumor, by the steps of:

(a) screening phage display peptides for their ability to bind specifically to a subtype of human GBM cell selected from (i) a highly invasive glioma cell (HIGC) subtype of human GBM cells of characterized by their ability to migrate from one brain hemisphere into which the cells are injected into the contralateral hemisphere, and (ii) a brain tumor initiating cell (wric) subtype of human GBM cells characterized by their stem-cell like properties of being able to self renew, generate spheres without the addition of exogenous mitogens and growth factors, and induce tumor formation in vivo when placed in the brains of immunocompromised mice, (b) further screening those peptides that are identified in step (a) for their ability to localize to cells associated with one of the two of human GBM cell subtypes in animal brain implants of the cells.

(c) further screening those peptides identified in step (b) for their ability to block the progression of GBM tumor in the animals, and (d) using a peptide from (c) in the diagnosis or treatment of human GBM tumor, or as a lead compound for diagnosis or treatment human GBM tumor.

Exemplary peptides identified in step (c) include SEQ ID NO: 7, for targeting HIGCs, or SEQ ID NO: 11, for targeting BTICs.

Also disclosed is a composition for delivering a neuropharmaceutical or agent anti-cancer agent to the brain. The composition is composed of the neuropharmaceutical or agent anti-cancer agent covalently conjugated to a carrier peptide that contains the sequence identified by SED ID NO: 7 and which is 12-20 amino acids in length.

These and other objects and features of the invention will become more fully apparent when the following detailed description of the invention is read in conjunction with the accompanying figures.

BRIEF DESCRIPTION OF THE FIGURES

FIG. 2A illustrates the inhibitory ability of the 12R library subclone H10 to selectively inhibit glioma invasion. Plating serial dilutions of phage with host bacteria on agarose plates was used to isolate phage subclones. Individual clones were isolated, amplified and tested for their inhibitory ability in in vitro invasion assays. The phage designated as H10 specifically and significantly blocked the migration of the invasive U87R cells through brain-like matrix coated transwell membranes (3×10$^{10}$ pfu; 4 hrs at 37T). Assessing the effects of LPS or random phage controlled for potential contamination by the host bacterial culture;

FIG. 2B shows that in addition to the H10 phage, the H10 synthetic peptide (50 uM) effectively and selectively inhibits migration of the highly invasive U87R cells, as well as the U87MG cells transfected with p75$^{NTR}$, a protein shown to mediate glioma invasion;

FIG. 2C demonstrates the clinical relevance of the H10 peptide, as the migration of 3/5 (60%) brain tumor initiating cell (BTIC) isolates from glioblastoma patients were inhibited by the H10 peptide. Asterisks indicate a statistically significant difference from untreated control; Dunnett's test ($p \leq 0.05$);

FIG. 4A shows accumulation of GM1 in the presence of H10. Invasive U87R cells were plated onto matrix-coated transwell membranes and incubated with H10 phage in the presence of Alexa 555-cholera toxin B subunit for 30 minutes to assess differences in the uptake and/or turn over of the lipid raft marker GM1. Cells treated with H10 showed a generalized accumulation of GM1 staining, characterized by globular internal structures and membranous localization (white arrows);

FIG. 4B are western blots showing that treatment of invasive glioma cells with H10 or cholesterol oxidase results in the accumulation of higher molecular weight complexes of p75$^{NTR}$, a membrane protein found in lipid rafts and known to promote cell migration. Density gradient fractions were prepared from U87R cells plated onto collagen and treated with PBS (control), H10 phage, F2 phage, or cholesterol oxidase for 2 hours, and analyzed by Western Blot for p75$^{NTR}$. White arrows indicate higher molecular weight p75$^{NTR}$-containing complexes. Lines underneath the figure indicate the fractions in which common organelles are generally found;

FIG. 4C shows that treatment of glioma cells with H10 results in accumulation of p75$^{NTR}$ at the plasma membrane. BTIC 25 cells (no GFP) were plated on matrix-coated transwell membranes and treated with phage for 2 hours. The p75$^{NTR}$ receptor, which is normally cleaved during p75$^{NTR}$ signaling, is greatly increased at the cell membrane after H10 treatment. p75$^{NTR}$ does not appear to accumulate in the H10-affected GM1 compartment, suggesting H10 may act on more than one class of membrane structure;

DETAILED DESCRIPTION OF THE INVENTION

I. Definitions

Figure 1A:
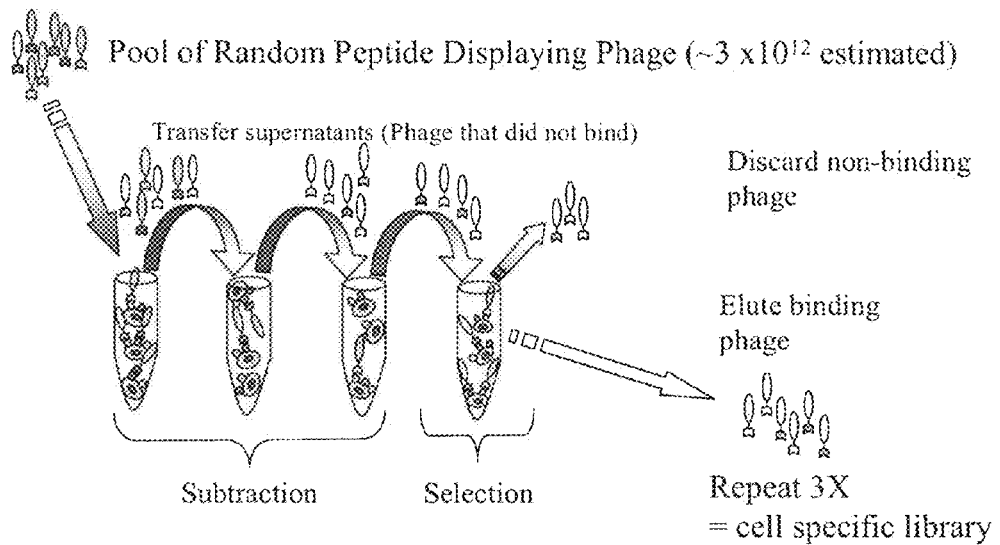
FIG. 1A is a schematic paradigm for the selection of phage that bound preferentially to the highly invasive glioma cell population developed by in vivo serial passage referred to as U87R. Peptide selection was performed in a two-step process using a series of biopanning steps where the PhD-12 M13 combinatorial phage display library was first subtracted for phage that bound to non-target cells, the non-invasive U87T cells, to remove any phage common between the cell types. Next, a positive selection was performed for phage that bound preferentially to the target cells, U87R. Any non-bound phage was discarded and the remaining phage were amplified in a series of steps that enriched for the target specific phage referred to as the 12R library.

"Human glioblastoma multiforme (GBM)" refers to the most common and aggressive type of primary brain tumor in humans. GBM tumors are characterized by the presence of small areas of necrotizing tissue that is surrounded by anaplastic cells (pseudopalisading necrosis). This characteristic, as well as the presence of hyperplastic blood vessels, differentiates the tumor from Grade 3 astrocytomas, which do not have these features.

"Highly invasive glioma cells," or "HIGCs," are a subtype (subpopulation) of human GBM cells characterized by an ability to migrate from one brain hemisphere into which the cells are injected into the contralateral hemisphere. An example of an HIGC is the U87R subtype of the U87MG human glioblastoma cells.

"Brain-tumor initiating cells," or "BTICs," are a subtype (subpopulation) of human GBM cells characterized by their stem-cell like properties of being able to self renew, generate spheres without the addition of exogenous mitogens and growth factors, and induce tumor formation in vivo when placed in the brains of immuno-compromised mice.

"Peptide-displaying phage" refers to bacteriophage that have been engineered to express a library, typically a combinatorial library, of exogenous peptides on their surfaces, allowing phage selection based on the presence on the phage surface of an exogenous library peptide.

"HIGC-specific peptides" refers to peptides, typically associated with peptide-displaying phage, that bind preferentially to HIGCs under the conditions of phage-display panning described in Section VIIIC below.

"BTIC-specific peptides" are peptides, typically associated with peptide-displaying phage, that bind preferentially to BTICs under the conditions of phage-display panning described in Section VIIID below.

Peptide-displaying phage "bind preferentially to HIGC's or BTICs" if the phage remain bound to immobilized HIGC or BTIC target cells under the phage-panning wash conditions described in Section VIM: and VIM, respectively, below.

Amino acid residues are indicated herein by their standard one-letter code (see, for example, www.mun.ca/biochem/courses/3107/aasymbols.html).

II. U87R-cell Specific Peptides

In accordance with the present invention, the invasive glioma and BTIC compartments have been newly modeled, allowing detailed examination of potential targetable components. The invasive glioma model described herein was developed by in vivo serial passaging of GFP neo-transfected U87MG human glioblastoma cells through mouse brains to isolate the invasive subpopulation (U87R, remote from primary tumor) from brain hemispheres that were contralateral to the injection sites [5, 6]. When cultured in vitro and compared to their non-invasive counterparts (U87T, tumor forming), these cells retained a higher propensity to invade both in vitro and upon reinjection into mouse brains. Microarray analyses showed that many genes were either down- or up-regulated in the U87R cells when compared to the U87T cells, including increased expression of $p75^{NTR}$. Using a combination of functional, biochemical, and clinical studies, it was found that $p75^{NTR}$ dramatically enhanced migration and invasion of genetically distinct glioma cells and frequently exhibited robust expression in highly invasive glioblastoma patient specimens [6]. These observations suggest that the U87R subpopulation is an appropriate model cell line for the subsequent peptide screening. The U87R subtype is an example of a highly invasive glioma cell (HIGC).

The BTIC model consists of a series of primary cell cultures derived from freshly resected human brain tumor specimens. Originating tumors are tested against a routine panel of antibodies to confirm a diagnosis of GBM, then subpopulations are selected via their ability to form self-renewing neurospheres in culture, as well as differentiate into astrocytic, oligodendrocytic or neuronal lineages. Upon injection of as few as ten cells into mouse brains, these brain tumor initiating cells (BTICs) tend to recapitulate the primary tumor as well as robustly invade, similar to what is seen with clinical GBM specimens [28]. Although unclear if BTICs are the best representation of brain cancer stem cells, they remain an excellent model for delineating the behavior of the human disease.

In accordance with the invention, peptides useful in targeting, characterizing and manipulating cells from disease reservoirs implicated in relapse of post-treatment GBM have been identified. The peptide selection was accomplished through phage display techniques already proven successful in other studies. For example, biopanning a phage display library against target cells or purified molecules has led to the characterization of cell surface proteins unique to defined cell subpopulations (e.g. the vascular address system [30, 31]), the identification of motifs important for specific protein function (e.g. the RGD motif necessary for integrin engagement [32-34]), as well as the isolation of peptide reagents with functional utility [35-38]. In practical terms, selection of unique phage displayed peptide sequences useful in diagnosis or therapy of patient glioblastomas can only be done ex vivo, necessitating the development of our unique, clinically relevant model systems, which recapitulate particular characteristics of GBM that cause therapeutic difficulties, allowing the causative cell types to be studied in isolation.

The final panels of selected peptides described herein have shown to be useful in demonstrating the molecular heterogeneity between cell populations and within a given cell population, and may lead to further refinement in the characterization of glioblastoma subtypes which will allow matching of tumor phenotypes with patient outcome, or with a particular therapeutic regimen, essential components of personalized medicine in cancer therapy. Alternately, because of the in vivo utility demonstrated, these peptides can be used as clinical imaging tools, or reagents for targeting chemotherapeutics to a particular tumor subtype. There is also inherent therapeutic potential of the unmodified peptides, as one of these dramatically inhibits the migration and invasive abilities of TAM cells as well as patient isolates that exhibit invasive properties.

Figure 1B:
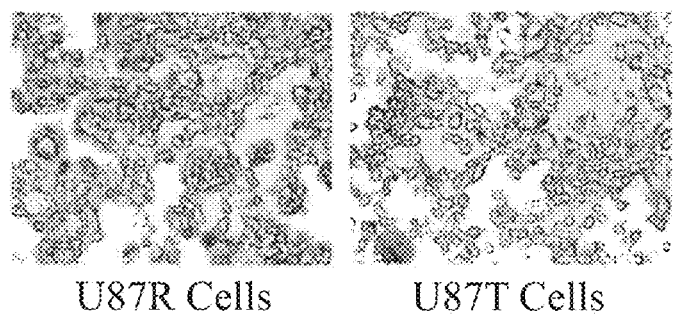
FIG. 1B shows a Whole cell ELISA assay that detects phage that is bound to the surface of the cells. The 12R phage library was incubated with the invasive U87R or non-invasive U87T cells, any non-bound phage were removed and an HRP-anti-M13 antibody and TMB substrate (blue) was used to detect bound phage. The 12R library preferentially bound to the highly invasive U87R cells.

A. Selective Biopanning of the Phage Display Library Resulted in the Isolation of a UM-specific Peptide Sequence that Inhibits Glioma Cell Migration The present inventors have earlier described an in vivo selection for a population of human glioma cells that were highly invasive (U87R) [6]. In order to isolate peptides that could bind specifically to these highly invasive glioma cells, a biopanning experiment using a combinatorial phage display library was employed. Initially subtractive biopanning was performed with the U87 cells that were non-invasive (U87T) followed by selective biopanning with the U87R cells to isolate a library of phage (FIG. 1A) that were confirmed to preferentially interact with U87R cells by whole-cell ELISA (FIG. 1B). These phage were subcioned by plating serial dilutions of phage with host bacteria on agarose plates, and the sequences of the peptide inserts were determined, and listed in Table 1, which shows, from left-to-right, (i) the peptide identifier, (ii) peptide sequence e, (iii) SEQ ID NO, and (iv) number cell-binding phages containing that sequence.

To select a phage subclone for further biochemical and in vivo evaluation, phage were tested for the ability to functionally affect the behavior of the U87R cells. The H10 phage-displayed sequence (SEQ ID NO:7) was found to abrogate the migration of the U87R cells through membranes coated with a brain-like extracellular matrix (FIG. 2A). Other phage peptides, e.g., M32 and M24, also showed a similar inhibitory trend as H10, although not as strong an effect. The possibility that bacterial components from the host culture could be causing the inhibition was ruled out by also testing the effects of LPS and a 20× volume of randomly selected phage. A synthetic version of the H10 peptide was also able to inhibit the migration of U87R cells, as well as U87 cells transfected with $p75^{NTR}$ (FIG. 2B), a molecule shown to be sufficient to confer a migratory phenotype in brain tumor xenografts [6]. These results confirmed the inhibitory property of this peptide in the absence of the phage particle.

TABLE 1

U87R-binding peptides

| | | | |
|---|---|---|---|
| A2 | SVSVGMKPSPRP | (SEQ ID NO: 1) | 21/100 |
| M32 | GISLSSYLQSTQ | (SEQ ID NO: 2) | 20/100 |
| C12 | EHMALTYPFRPP | (SEQ ID NO: 3) | 13/100 |
| M5 | HWAPSMYDYVSW | (SEQ ID NO: 4) | 7/100 |
| M43 | RTVPDYTAHVRT | (SEQ ID NO: 5) | 5/100 |
| M19 | SGHQLLLNKMPN | (SEQ ID NO: 6) | 4/100 |
| H10 | TNSIWYTAPYMF | (SEQ ID NO: 7) | 3/100 |
| F2 | GMSLSRQMLWSL | (SEQ ID NO: 8) | 2/100 |
| M24 | HLFPQSNYGGHS | (SEQ ID NO: 9) | 2/100 |
| M23 | CIQLANPPRLXG | (SEQ ID NO: 10) | 2/100 |

The global utility of the H10 peptide was tested in the transwell assay by using BTIC lines established from individual patient specimens. As these were isolated directly from resected tumors, it was felt they would give an indication of the true clinical potential of H10. The migration of 60% (3/5) of the BTIC lines tested was significantly inhibited, although all five showed an inhibitory trend (FIG. 2C). In experiments where H10 had no significant effect, the cells were not highly invasive to begin with.

B. H10 Affects the Turn Over of GM1-containing Structures and Other Lipid Raft Components To determine the molecular mechanism by which the H10 peptide is inhibiting glioma invasion, a biotinylated version of the peptide was used to pull down potential binding partners which were then analyzed by mass spectrometry. Many of the proteins detected had some role or association with endosomal or vesicular transport (Table 2).

Figure 3B:
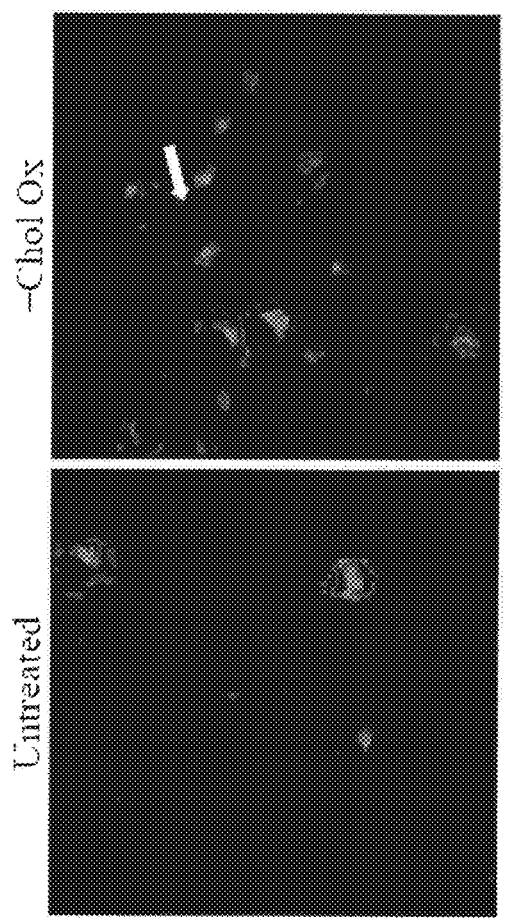
FIG. 3B shows that cholesterol oxidase prevents internalization of a lipid raft marker GM1. U87R cells were plated onto matrix-coated transwell membranes and treated with cholesterol oxidase and Alexa 555-cholera toxin B subunit for 120 minutes to assess differences in the uptake and/or turn over of its receptor, GM1. The white arrow indicates a membranous accumulation of GM1.
Figure 3A:
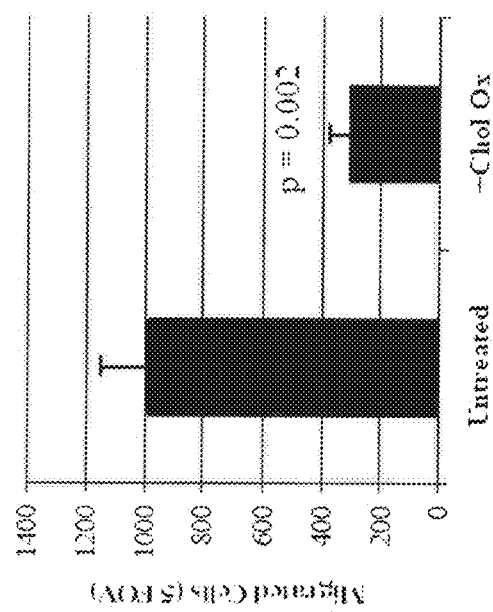
FIG. 3A is a bar graph showing that cholesterol oxidase inhibits cell migration. The invasive U87R cells were plated on matrix-coated transwell membranes and treated with cholesterol oxidase (1.8 U/mL) for 4 hours. Cells that migrated to the underside of the transwell membrane were stained with crystal violet and counted by light microscopy.

As lipid rafts are involved in some endocytotic processes [39-44], the reactions of the U87R cells to treatment with cholesterol oxidase, a known lipid raft disruptor [45, 46], was examined. Cell migration was abrogated in the transwell assay (FIG. 3A), and GM1, a component of both non-caveolar lipid rafts and caveolae [47, 48], was seen to accumulate within the cells, particularly at the plasma membrane (FIG. 3B). Similar effects were seen when cells were treated with H10, in comparison to a control phage, in three independent cell lines (FIG. 4A).

TABLE 2

Mass Spec Hits of Interest

| Focal Adhesions/CSK Reorganization: | LIM Domain Containing Proteins: | Endosomes/Vesicle Transport: | Plasminogen Receptors: |
|---|---|---|---|
| ESP-2 | Zyxin | RAB1B | Alpha-enolase |
| Zyxin | ESP-2 | RAB1A | Annexin A2 |
| Gamma-filamin | TRIP6 | MEL | |
| Transgelin 2 | Lasp-1 | REB35 | |
| IQGAP1 | ABP-278 | Rab-15 | |
| TRIP6 | | TIP47 | |
| Lasp-1 | | Clathrin | |
| ABP-278 | | Transferrin Receptor Protein 1 | |
| Talin 1 | | Transmembrane protein 33 | |
| | | Glyceraldehyde-3-phosphate dehydrogenase | |
| | | SEC13 | |
| | | Coatomer protein complex | |

The p75 neurotrophin receptor (NTR) can be detected differentially in lipid rafts isolated with specific detergents [49]. Alternately, intracellular vesicles can deliver molecules required for a particular function to the polar extremes of a cell, for example, transport of digestive enzymes or structural molecules such as integrins to the leading edge during migration [50-52].

Figure 9A:
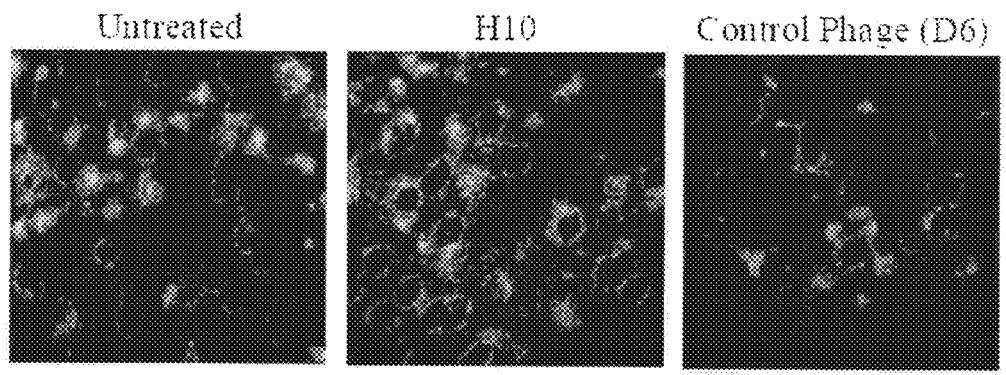
FIG. 9A are confocal images of p75$^{NTR}$ transfected glioma cells (U87p75) imaged for uptake of FITC-transferrin. U87p75$^{NTR}$ grown in the presence of H10 and cholesterol oxidase were assessed for FITC-transferrin uptake 2 hours after cells were plated on collagen-coated transwell membranes. H10 and cholesterol oxidase had no effect on distribution of transferrin or transferrin receptor, markers of clathrin-coated vesicles.
Figure 9B:
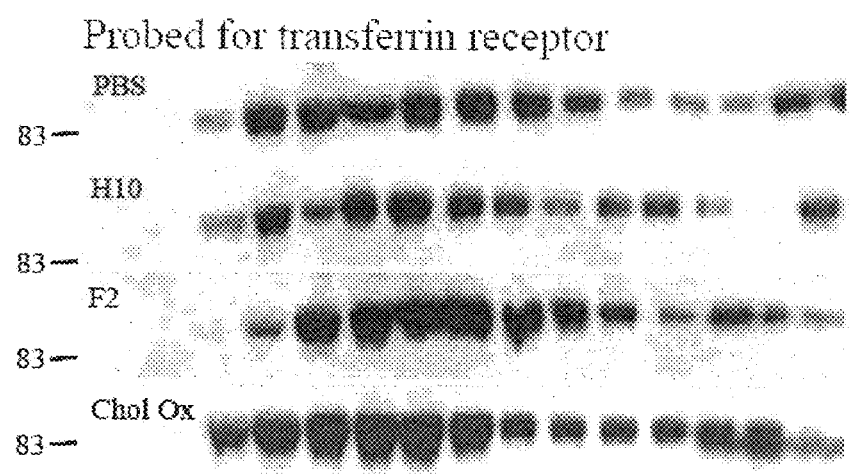
FIG. 9B shows cellular fractionation of invasive U87R cells using iodixanol gradient separation. U87R cells were treated with H10, F2, cholesterol oxidase or control PBS for two hours. Cells were lysed, fractioned using an iodixanol gradient, and Western Blot analysis for the transferrin receptor was performed.
Figure 10A:
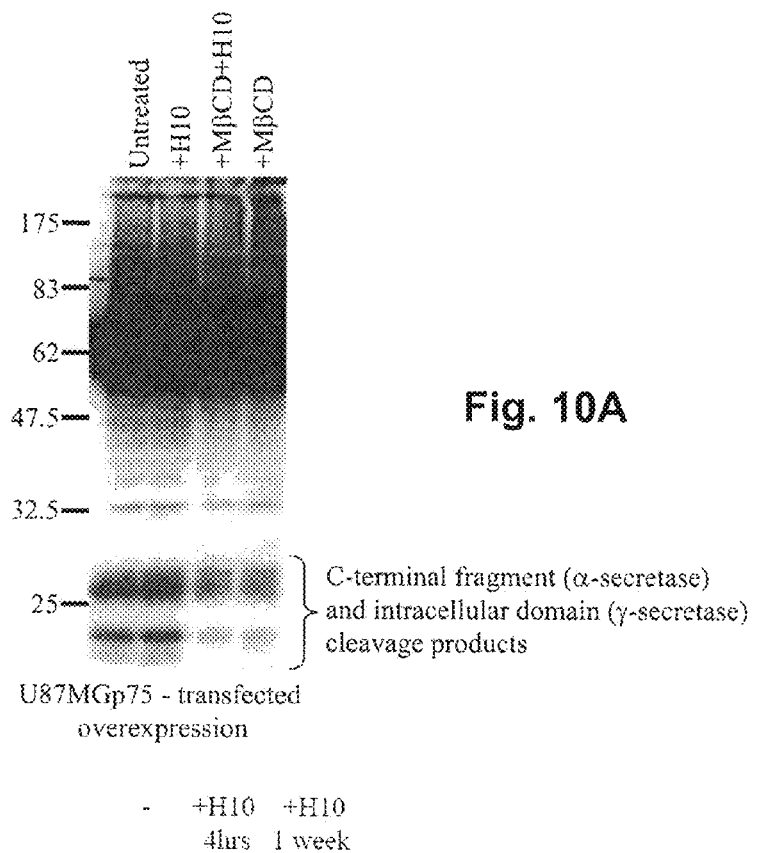
FIG. 10A shows an anti-p75$^{NTR}$ Western blot and full-length p75$^{NTR}$, the C-terminal fragment (a-secretase) and intracellular domain (γ-secretase) cleavage products were visualized after treatment with H10, MbCD or H10+MbCD.
Figure 10B:
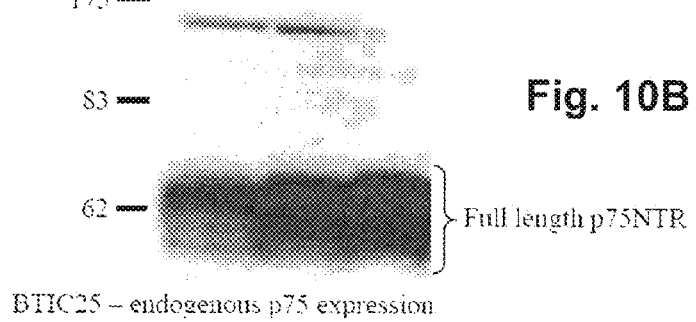
FIG. 10B shows Western Blot analysis of full-length p75$^{NTR}$ after exposure to H10 for 4 hours and 1 week.
Figure 10C:
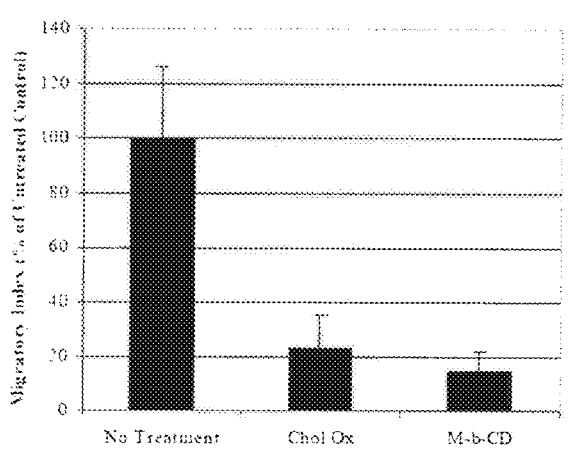
FIG. 10C shows in vitro invasion assays performed in the presence of cholesterol oxidase and methyl-β-cyclodextran. Both cholesterol oxidase and methyl-β-cyclodextran significantly inhibited cell migration of U87p75 glioma cells.
Figure 11:
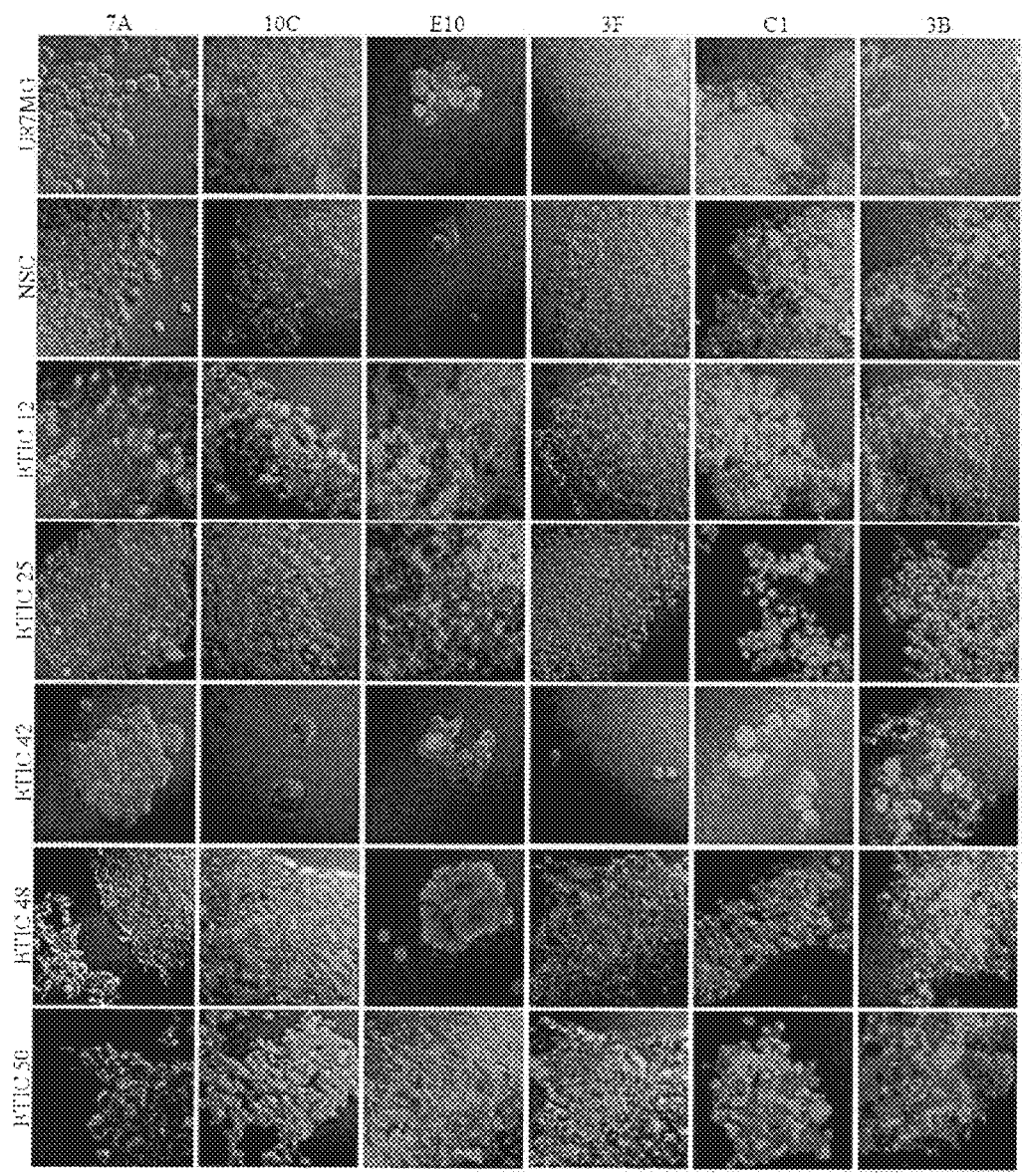
FIG. 11 shows confocal images of a panel of patient-derived RTIC isolates (rows) that have been screened for binding specificity to a number of biotinylated synthetic peptides (red; columns).
Figure 12A:
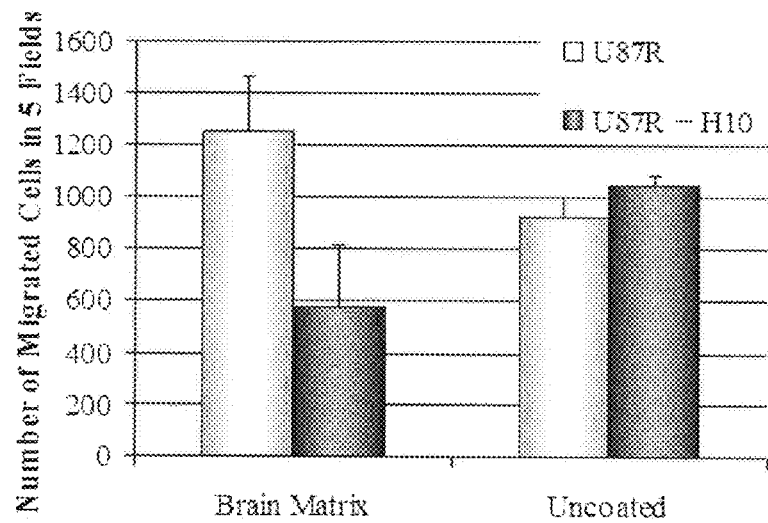
FIGS. 12A and 12B show in vitro transwell migration assays in the presence of different extracellular matrices. The presence of brain matrix was essential for H10-mediated abrogation of cell migration in vitro (FIG. 12A), with collagen I mediating the majority of the effect (FIG. 12B).
Figure 12B:
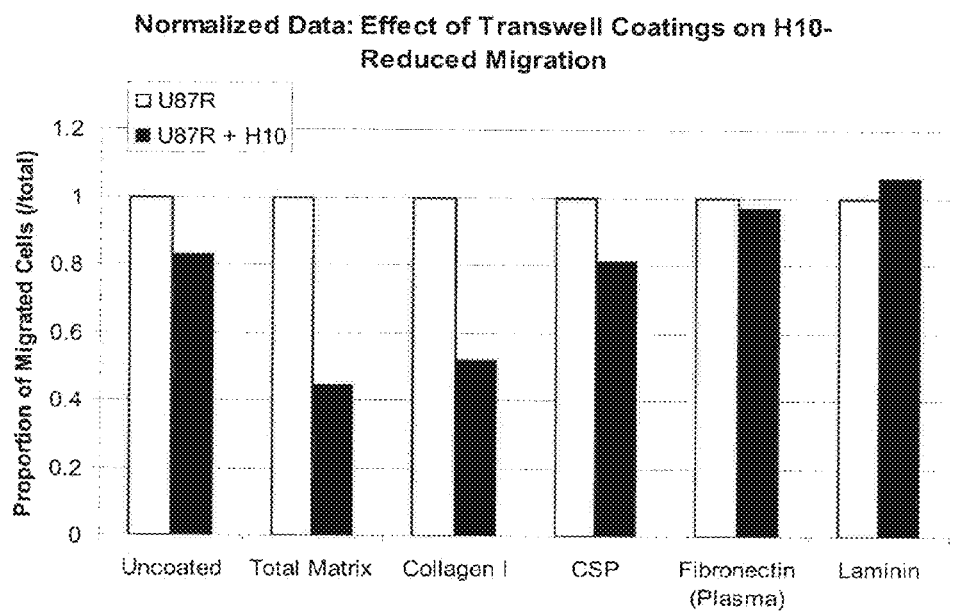

The $p75^{NTR}$ can be detected differentially in lipid rafts isolated with specific detergents [49], and must be proteolytically processed to trigger cell migration in glioma cells [5]. Thus, it is probable that $p75^{NTR}$ is also cleaved within a lipid raft after endocytosis [53]. To determine if H10 may be having an impact on endosomally located $p75^{NTR}$, cells were hypertonically lysed (to keep vesicles and organelles at least partially intact) and separated on a 10-40% sucrose/iodixanol gradient from which fractions were individually collected. Both H10 and cholesterol oxidase resulted in a shift of higher molecular weight forms of $p75^{NTR}$ into the denser gradient fractions (FIG. 4B). While the majority of $p75^{NTR}$ does not appear to be associated with GM1-containing lipid rafts, incubation of the cells with H10 did cause increased co-localisation of the $p75^{NTR}$ intracellular and extracellular domains (FIG. 4C). Taken together, the data suggests that (i) 1110 can inhibit the turn over of both GM1 and $p75^{NTR}$-containing lipid rafts and (ii) H10 appears to be preventing the release of at least a portion of the $p75^{NTR}$ extracellular domain produced within a cell. In contrast, H10 and cholesterol oxidase have no effect on the intracellular localization or gradient fractionation of transferrin or its receptor, which are markers of clathrin-coated vesicles (FIGS. 9A and 9B), and while H10 does not show an obvious effect on the processing of over-expressed transfected $p75^{NTR}$, it may cause a slight accumulation of endogenously expressed full length protein (FIGS. 10A-10C).

III. BTIC-cell Specific Peptides

A BTIC-specific phage library was generated as described for the 12R library, using U87MG cells, U251N cells, and human normal fetal astrocytes as subtraction cells to deplete the library of background phage, and a mixture of BTIC isolates (BTIC 12, 25, 42, 50) from different patients for the selection.

A. Peptides from Phage Biopanned Against BTIC Isolates Reveal Heterogeneity within Cultured Neurospheres.

The most abundant phage that was isolated was called 7A (25/50) and encoded the 12-mer sequence N-PSPHRQRQII-ILR-C (SEQ ID NO: 11). In addition, 5 other independent phage (10C, E10, 3F, C1 and 38) were isolated more than once and comprised 50% (25/50) of the subclones screened, shown in Table 3.

Figures 7, 8:
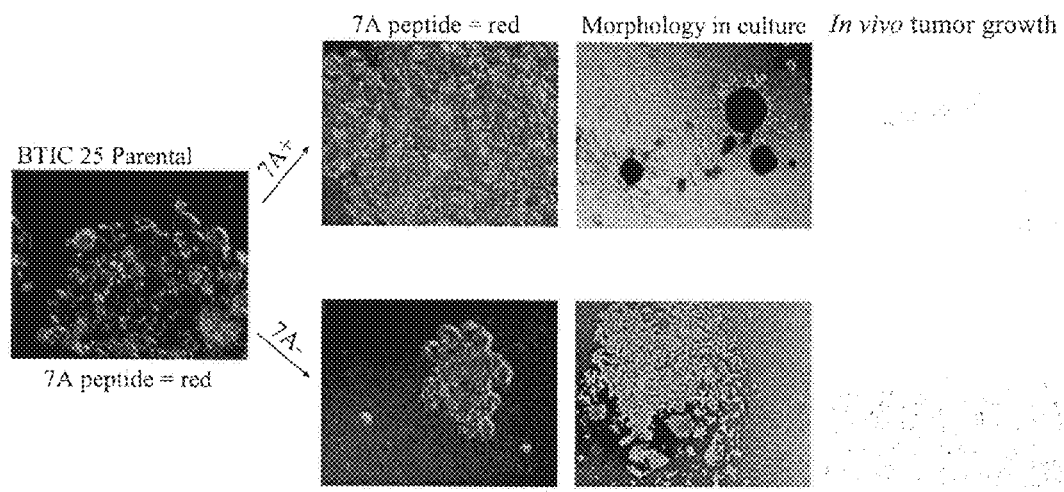
FIG. 7 demonstrates that the 7A peptide can distinguish subpopulations within a BTIC isolate with defined cellular behavior. BTIC25 was subcloned by limiting dilution and screened for binding to biotinylated 7A peptide (red). Subpopulations that hound to 7A had a higher propensity to form neurospheres in culture, were not highly proliferative as a xenograft in SCID mice, and were found preferentially near the ventricles. Human xenografts were implanted in the right brain hemisphere of mice and visualized by an antibody to a human nuclear antigen (brown). Sections were counterstained with Toluidine blue to visualize all cell nuclei.
FIG. 8 is a table showing binding specificities of BTIC-selective peptides on a representative selection of BTIC isolates.

To confirm the preferential binding of 7A to the BTICs rather than the cells used for subtraction, neurospheres and U87MG cells were stained in suspension with biotin-labeled synthetic peptide. Two of the BTIC lines showed a high percentage of positive cells within the neurosphere, while normal stem cells (not tumorigenic and not used in the depletion or selection) and U87MG cells were predominantly negative, as expected (FIG. 5B). Examination of the interaction of all selected peptides across a panel of BTIC lines underscored the heterogeneity within each cell population, and established a platform for correlating the ability to bind particular peptide sequences with either cell behavior or patient outcome. FIG. 8 shows binding specificities of BTIC-specific peptide hits on a representative selection of BITCs.

TABLE 3

BTIC-binding peptides

| 7A | PSPHRQRQHILR | (SEQ ID NO: 11) | 25/50 |
| 10C | QTIRIIIRRSRT | (SEQ ID NO: 12) | 6/50 |
| E10 | SLHMRHKRKPRR | (SEQ ID NO: 13) | 4/50 |
| 3F | SSRSMQRTLIIS | (SEQ ID NO: 14) | 2/50 |
| C1 | IRSIRMRRILIL | (SEQ ID NO: 15) | 2/50 |
| 3B | KTSMRPLILIHI | (SEQ ID NO: 16) | 2/50 |

IV. Homing Properties of the U87R and BTIC Binding Peptides

Figure 6A:
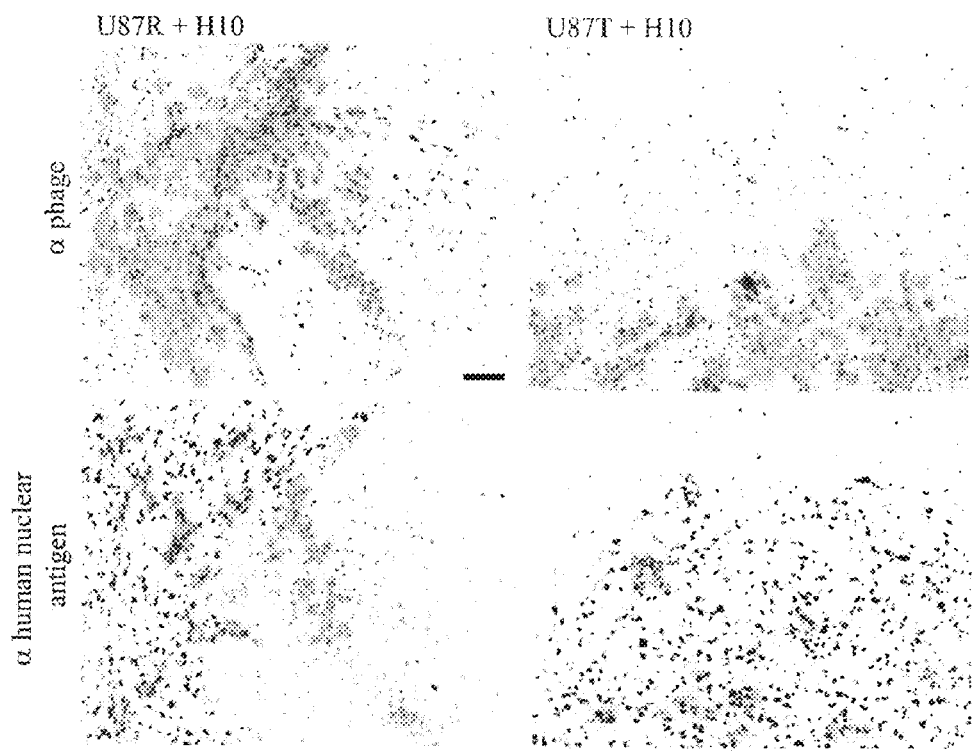
FIG. 6A illustrates the in vivo homing capability of H10. Invasive U87R or non-invasive U87T cells were grown in the right brain hemisphere of SCIT) mice. Once tumors were established, mice were anaesthetized and perfused with H10 phage for 10 minutes. Unbound phage was flushed from the system with PBS. Brains were cryosectioned and immunohistochemically stained for M13 phage or human nuclear antigen (hNA). In comparison to the tumors established using the U87T cells, the H10 phage homed more efficiently to the U87R tumor cells as demonstrated by increased staining on the U87R cell bodies and along the edge of the xenograft mass.

The ability of the selected phage or their corresponding peptides was examined for their ability to 'home' to their respective U87R or BTIC glioma cell targets in vivo, according to their ability to detect glioma cells in an orthotopic xenograft model. In the case of H10, SCID mice carrying U87R or U87T xenografts were injected with the test phage for ten minutes, which was subsequently perfused with PBS to remove any unbound particles. Serial sections of the brains were immunohistochemically stained for M13 phage, demonstrating that H10 homed specifically to the U87R, but not the U87T tumors (FIG. 6A).

Figure 6B:
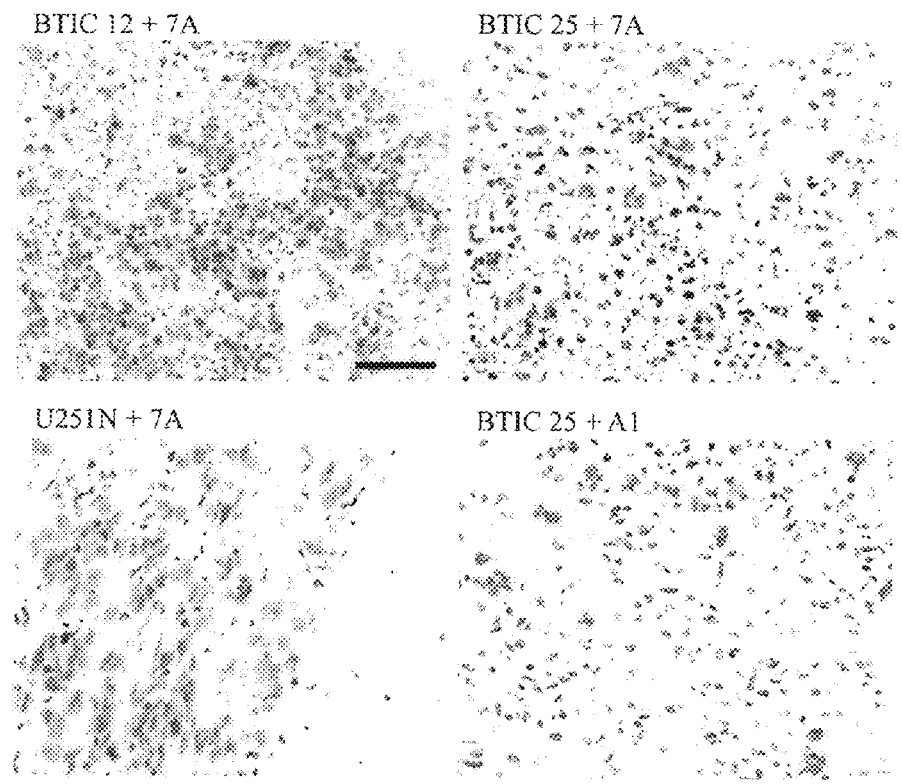
FIG. 6B shows that 7A homes in vivo to BTIC12 and BTIC25 xenografts. Cells were injected into the right brain hemisphere of SCID mice and allowed to establish for three months. Mice were then perfused with 7A or A1 (random control) phage for 10 minutes. The distribution of phage binding was unique between the two BTIC xenografts and again reveals heterogeneity within the samples. 7A homing was not observed in mice bearing tumors generated from the U251N cell line. Perfusion of a BTIC 25 xenograft with a randomly selected phage, A1, showed minimal staining.

To determine if 7A would also demonstrate binding specificity to a subset of cells within neurospheres in vivo, SCID mice carrying BTIC xenografts were injected with 7A phage, and the brains cryosectioned for anti-phage immunohistochemistry. As seen with ex vivo staining of neurospheres, only a subset of cells within the main tumor masses of BTIC 12 and 25 showed positive staining (FIG. 6B). Additionally, no staining was detected in the surrounding tissue as well as in xenografts made of non-target cells, specifically the U251N human glioblastoma line. Perfusion of a BTIC 25 xenograft with a control phage (A1, randomly selected subclone) Showed minimal staining, again confirming the selectivity and binding specificity of the 7A displayed peptide.

Figure 5:
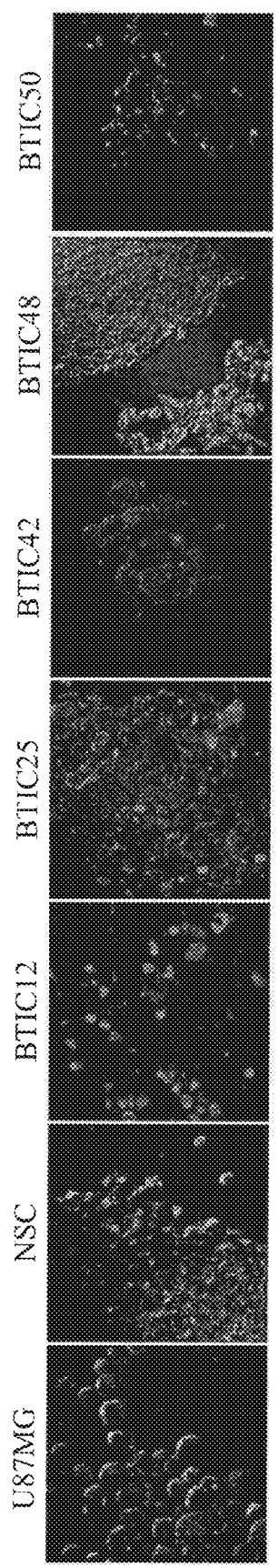
FIG. 5 shows single Z-stack projections from confocal micrographs of BTIC isolates stained with biotinylated 7A peptide. Binding specificity of the 7A peptide was assessed with non-target (U87MG; NSC) and target (BTIC) cells using a biotinylated 7A peptide (red) followed by confocal imaging.

The studies reported above indicate that 7A phage/peptide recognizes only a subset of cells within an individual BTIC line (FIG. 5, FIG. 6B). It was therefore of interest to determine whether there were unique properties of these cells of which 7A binding may be an indicator. The BTIC 25 cells were subcloned by limiting dilution and screened for peptide binding. The population of cells enriched for 7A binding was distinctly different from the non-binding counterparts, forming neurospheres in culture as opposed to adherent colonies (FIG. 7). Additionally, the 7A binding subpopulation did not proliferate well in orthotopic xenografts (3 months growth time), and could only be detected in small numbers within the subventricular zone of the brain, a region in the brain known to host a neural stem cell niche. The 7A non-binding subpopulation were very tumorigenic and formed very large tumor masses with limited invasion into surrounding tissue. Therefore, the 7A peptide distinguishes a population of cells associated with neurosphere formation, low proliferative activity in vivo, and a preference to locate within the subventricular zone. The fact that both populations were derived from a BTIC culture indicates that 7A is able to track the progression of cells within this reservoir from hidden precursor to recurred tumor.

V. Peptide Composition and Peptide Conjugates

In one aspect, the invention includes a peptide composition for targeting either (i) a highly invasive glioma cells (HIGC) subtype of human GBM cells, e.g., the U87R subtype of U87GM cells, or (ii) a brain tumor initiating cell (BTIC) subtype of human GBM cells, as characterized above. The peptide in the composition is 12-20 amino acid residues in length and contains one of the sequences identified as SEQ ID NOS-1-16, or a sequence that is at least 90% homologous with the given sequence. That is, the peptide has the same sequence as one of SEQ ID NOS: 1-16, or a sequence that differs from the given sequence by at most one amino acid residue. The peptide may contain only the given sequence of amino acids, or may contain additional N- and/or C-terminal residues up to a total of 20 residues. Thus, for example, the peptide corresponding to SEQ ID NO: 7, TNSIWYTAPYMF (H10), may have this exact sequence, the same sequence but with a single amino acid substitution, addition or deletion at any of the 12 residue positions, or a peptide having a total of up to eight additional residues at one or both of the N- or C-terminals.

A. Peptides

The peptide of the invention is formed by conventional solid-phase or recombinant DNA synthetic methods, using amino acids having the natural L-isomer form, the D-amino acid form, or a mixture of the two. Peptides having an all D-form or partial D-form composition are expected to be more resistant to proteolytic breakdown under biological conditions, e.g., when administered to a patient. Solid-phase peptide synthesis methods for preparing peptides composed of all L-amino acids, all D-amino acids or a mixture of D- and amino acids utilizing activated D- or L-form amino acid reagents are described, for example, in Guichard, G., et al., Proc. Nat. Acad. Sci. USA Vol. 91, pp. 9765-9769, October 1994). Alternatively, the peptides may be composed of D-amino acids synthesized in a reverse-sequence direction, that is, in a carboxy to amine end direction, to produce a so-called retro-inverso (RI) pilin peptide. Methods for synthesizing RI-form peptides are detailed, for example, in Fletcher, M. D. and Campbell, M. M., Partially Modified Retro-Inverso Peptides: Development, Synthesis, and Conformational Behavior, Chem Rev, 1998, 98:763-795, which is incorporated herein by reference.

For use in targeting HIGCs, the peptide contains a sequence selected from the group consisting of SEQ ID NOS: 1-10, preferably SEQ ID NOS: 2, 7, and 9, of which SEQ ID NO: 7 is exemplary. For use in targeting BTICs, the peptide contains a sequence selected from the group consisting of SEQ ID NOS: 11-16, preferably SEQ ID NOS: 11, 13, and 16, or which SEQ ID NO: 11 is exemplary.

B. Peptide Conjugates and Composition.

For use as a diagnostic reagent, for detecting HIGC or BTIC subtypes in a patient with a human GBM tumor, the peptide may be conjugated to a radioimaging or other detectable moiety, such as fluorescent or other photo-emitting moiety. Major imaging technologies that presently utilize imaging agents include x-ray/Computed Tomography (CT), Magnetic Resonance Imaging (MRI), Positron Emission Tomography (PET), Single Photon Emission Computed Tomography (SPECT), and ultrasound technologies. Among widely used radio-imaging agents are gadolinium-based imaging agents, technetium-based agents, and radio-iodinated agents. The radio-imaging agent or coordination complex carrying a radio-isotopic metal, may be covalently attached to the peptide according to well known methods, e.g., through a covalently attached ligand coordination complex.

For use as a therapeutic agent, to inhibit or destroy HIGC or BTIC cells specifically, the peptide may be conjugated to one or a variety of anti-minor agents, including, for example, alkylating agents, anti-metabolites, plant alkaloids mad terpenoids, e.g. TAXOL, topoisomerases, proteasome inhibitors, and monoclonal antibodies. The anti-tumor agents may be covalently attached to the peptide according to well-known methods.

In still another embodiment, the peptide of the invention is formed as a fusion peptide with a peptide carrier, such as angio-pep-2 or angiopep-7 (SEQ ID NOS: 17 and 18, respectively) that is capable of facilitating passage of the peptide across the blood brain barrier (BBB) (62).

The composition of the invention may include (i) the peptide alone, (ii) the peptide in a suitable carrier, e.g., sterile physiological saline, in liquid or dried form, (iii) the peptide in conjugated form as described above, or (iv) the peptide formulated in a suitable peptide-delivery nanoparticle, such as encapsulated within nanoparticles of poly(lactide-co-glycolide) copolymer, cyclodextrin nanoparticles, or cetyl alcoholipolysorbate. Nanoparticles useful for delivering drugs across the BBB barrier are well known in the art (e.g., 68-71). The nanoparticles are preferably in the 30-100 nm size range and may be coated with polyethyleneglycol for enhanced circulation time in the bloodstream. The particles may be suspended in an injectable medium, e.g., sterile physiological saline, or supplied in dehydrated form.

C. Carrier Peptide

Immunohistochemical staining of mouse brains carrying U87R tumors that had been perfused with H10 phage showed positive signal that was either localized within the tumor mass or peritumoral, demonstrating that H10 has the ability to cross the blood brain barrier (BBB). This feature is exploited, according to another aspect of the invention, in a novel composition comprising a conjugate of the H10 peptide, as a carrier peptide, and a neuropharmaceutical or anti-cancer agent that is to be delivered to the brain. The agent may include any pharmaceutical agent used, or potentially useful, in treating a neurological condition, such as depression, anxiety, schizophrenia, hyperactivity, Alzheimer's disease, or Parkinson's disease, or any anti-tumor compound, such as from the classes named above, that would be effective against cancers of the brain or spine if the blood brain barrier could be breached. The agent is conjugated to the peptide according to known methods, such those involving direct attachment of the compound to an activated hydroxyl, sulfide, amine or carboxyl groups on the peptide or attachment of the peptide to a corresponding activated group on the compound, or by the use of a bifunctional coupling reagent.

VI. Diagnostic and Therapeutic Methods

Research into GBM has expanded from the biology of developed tumors into the subsets of cells currently believed to be the initiators and disease reservoirs for these tumors. The current view is that any given brain tumor consists of a mixture of cells with varying stages of "sternness" or differentiation, with each subpopulation retaining inherent potentials to contribute to relapse [1, 54]. New microarray data have begun to better delineate profiles for predicting patient outcome, and the nature of recurrent disease [1]. It is becoming evident that not all of these subpopulations are treatable by current therapeutics, ultimately resulting in relapsed disease. Further complicating the scenario, these cell populations may also be stimulated by chemo- and radiotherapy to evolve into more aggressive phenotypes [55, 56]. One goal of the present invention is to contribute to the practical solution of eliminating the identified subtypes of GBM and associated disease reservoirs.

To that end, the invention provides methods for diagnosis and/or treating patients with human GBM tumors, and in particular, provides an improvement in the treatment of GBM tumors in human patients, by characterizing and/or treating subpopulations of tumor cells that are likely causes of tumor recurrence. The patient may have been previously treated with one or more known treatment modalities, such as chemotherapy, x-radiation therapy and/or surgical resection. The initial treatment may cause a significant reduction in tumor size or growth, but the tumor may likely recur due to the presence of a HIGC subpopulation of cells that may reside outside the treatment region, or through a BTIC subpopulation of cells capable of reseeding the tumor with actively dividing GBM cells.

In practicing the method, the peptide composition of the invention is administered to the patient in a diagnostically sufficient amount or therapeutically effective amount, allowing the oncologist to (i) to identify the presence of HGIC and/or BTIC subtype cells in the brain, e.g., by using the peptide of the invention for radio-imaging, and (ii) to use the peptide, either alone or conjugated with an anti-tumor agent, to kill or inhibit the growth or migration (in the case of HGICs) of the tumor subtypes, to reduce the risk and rate of tumor recurrence. That is, localization of the peptide composition at the targeted HIGC and/or BTIC cells, after administration to the patient, allows (i) the presence of cells of the targeted subtype to be detected, where the peptide composition includes a detectable radioimaging agent conjugated to the peptide, (ii) targeted HGIC or BTIC cells to be inhibited or destroyed, where the peptide composition includes an anti-cancer agent conjugated to peptide, and (iii) migration of HGIC cells toward a tumor site to be inhibited by the presence of the peptide alone.

A number of delivery system are available for delivering the peptide composition to the brain (62-71). As noted above, the H10 peptide is itself able to pass the blood brain barrier, and so may be administered by any systemic route including intra-arterial, IV, IM, subQ, nasal, mucosal or through the lungs, either as a peptide alone or peptide conjugated to an imaging or an anti-tumor agent.

Other available strategies for CNS delivery may be broadly classified as either invasive (neurosurgical-based), such as convection-enhanced delivery (66), pharmacologic-based, or physiologic-based (63). Neurosurgical-based strategies include intraventricular drug infusion, intracerebral implants, and BBB disruption. Pharmacologic-based strategies include the use of nanoparticle carriers (described, for example, in 68-71). Physiologic-based strategies take advantage of the normal, endogenous pathways of either carrier-mediated transport of nutrients or receptor-mediated transport of peptides.

In the latter category, Drappatz et al, conducted a Phase I study of ANG1005 in patients with recurrent glioblastomas. ANG1005 consists of three paclitaxel molecules linked to a novel peptide, Angio-Pep-2, that allows it to be transported across the blood-brain barrier via the low-density lipoprotein receptor-related protein 1 receptor (62). Angio-pep-2 is 19-amino acid peptide (SEQ ID NO: 17) that binds to low density lipoprotein receptor-related protein (LRP) receptors at the BBB and has the potential to deliver drugs to brain by receptor-mediated transport. Here the BTIC- or HIGC-specific peptide, with or without associated radio-imaging or anti-tumor agent, is conjugated to the Angio-pep peptide, and delivered by a systemic route.

Alternatively, after completing surgery to remove the primary tumor, the composition of the invention can be administered either directly in wafers or by installing a convection enhanced delivery pump to deliver the peptides on a routine schedule. Convection-enhanced delivery (CED) uses an infusion catheter whose tip is placed close to the target site. In this technique, a cannula is inserted directly into the area of the brain to be treated, and the therapeutic agent is delivered through the cannula via bulk flow, circumventing the BBB.

The peptide composition could alternatively be administered after brief disruption of the BBB using mannitol or other BBB disruption agent. This approach has recently been used to deliver Avastin to the brain tumors of patients (67).

Still another delivery method uses nasal transport routes via the olfactory nerve pathway (axonal transport) and the olfactory epithelial pathway.

As indicated above, the diagnostic method is carried out to image reservoirs of BTICs and/or HIGCs, typically after an initial treatment of the GBM tumor, e.g., by surgery, radiation therapy or chemotherapy. Depending on the resolution in visualizing targeted cells, the dose of diagnostic composition administered to the patient, or the route of administration, may be varied until a meaningful diagnostic result is obtained.

After identifying reservoirs of either cell type, the patient may be treated with the peptide in therapeutic form, to knock out or reduce populations of the reservoir cells. During this treatment, progress in reducing HIGC or BTIC populations can be checked periodically with the diagnostic method, and the therapeutic dose of the composition may be varied, if necessary, to increase the extent of inhibition or destruction of the targeted HIGCs or BTICs. Treatment is continued, e.g., by twice weekly or weekly administration of the composition, until a desired endpoint is observed.

VII. Screening Methods

Also disclosed are screening methods for identifying peptide compounds useful in the diagnosis or treatment of a human glioblastoma multiforme ((iBM) tumor, and screening methods for identifying new subtypes of HIGCs and BTICs.

In the method for identifying peptides capable of targeting GBM subtypes, phage-display peptide libraries are first screened for their ability to bind specifically to a subtype of human GBM cells, including (i) a brain tumor initiating cells (BTICs) subtype of human GBM cells characterized by their stem-cell like properties of being able to self renew, generate spheres without the addition of exogenous mitogens and growth factors, and induce tumor formation in vivo when placed in the brains of immunocompromised mice. and (ii) a highly invasive glioma cells (HIGCs) subtype of human GBM cells of characterized by their ability to migrate from one brain hemisphere into which the cells are injected into the contralateral hemisphere.

The peptides identified from the initial screening are further screened to identify peptides for their ability to localize to cells of the associated subtype of human malignant glioblastoma cells in animal brain implants of the cells. These peptides, in turn, are further screened their ability to block the progression of glioblastoma tumor growth in the animals. The peptides so identified are used in the diagnosis or treatment of human GBM or as lead compounds for diagnosis or treatment the human GBM.

The peptides identified in the above method, including those reported above, may in turn be used to identify new subpopulations of these two cell types, according to another aspect of the invention. The new avenues opened by use of the BTIC cell lines are of special interest because of the current questions surrounding whether or not a definitive brain stem cell marker has been identified. Several lines without the originally described stem cell marker, CD133, have been found that still retain self-renewal ability and pluripotency [27], while other differentiated tissues also express CD133 [26].

In this aspect of the invention, the 7A peptide or other BTIC-binding peptides are labeled, e.g., with a fluorescent label, and used to probe subpopulations of GBM tumor cells, such as cells in an expanded cell line, e.g., the U87MG cell line, or cells obtained from new patient GBM tumors. The method can be carried out by standard methods in which cells grown in culture are exposed to the labeled peptide reagent, e.g., fluorescent-labeled peptide. After washing, the labeled cells are isolated, e.g., by FACS, and the labeled cells further characterized, e.g., by surface antigen composition, to identify potential new subtypes of GBM. New subtypes, in turn, can be used in the above screening method to identify novel peptides that are specific for that subtype.

The experimental procedures described below are exemplary, and in no way intended the scope of the invention as defined by the claims, VIII. Experimental Procedures:

All animal experiments were conducted in accordance with the approval documents provided by the University of Calgary Ethics Board and Animal Care Facility. Tumor and normal tissues including the isolation of brain tumor initiating cell from banked patients samples were obtained from the Tumor Tissue Bank in Foothills Hospital, Calgary, Alberta.

A. Cell Culture:

The human glioma cell line U87 was obtained from the American Type Culture Collection, transfected with GFP and separated into the U87T and U87R subpopulations as previously described [6]. The human glioma cell line U251N and human fetal astrocytes were a kind gift from V. W. Yong (University of Calgary, Calgary, Alberta, Canada). All cells were maintained in complete media (Dulbecco's modified eagle's medium [DMEM] supplemented with 10% heat-inactivated fetal bovine serum [FBS], 0.1 mM nonessential amino acids, 2 mM L-glutamine, 1 mM sodium pyruvate, and transfected cells with 400 µg/ml of G41.8 (Invitrogen) at 37° C. in a humidified 5% $CO_2$ incubator. Cells were passaged by harvesting with trypsin (Gibco BRL) at 80%-90% confluence.

Brain tumour initiating cells (BTICs) were supplied by the BTIC Core Facility, maintained by Drs. Greg Cairncross and Samuel Weiss, after isolation by Dr. John Kelly [28] and maintained in NeuroCult media (Stem Cell Technologies) as neurospheres. Subcloning of the BTIC25 line into 7A positive and negative populations was done by limiting dilution.

B. Bacteriophage Culture:

The Ph.D.™-12 Phage Display Peptide Library Kit (New England Biolabs) was used as per manufacturer's protocol. Briefly, phage libraries were amplified as follows: Overnight cultures of the bacterial host strain ER2738 were diluted 1/100 in LB broth with 20 μg/mL tetracycline and inoculated with 10 μL of phage (~$10^8$-$10^{10}$ pfu/μL), then cultured with shaking at 37° C. overnight. Bacteria were pelleted and the phage were precipitated from the supernatant by adding 1/6 volume of 20% w/v PEG-8000, 2.5M NaCl and storing at 4° C. overnight, followed by centrifugation for 15 minutes at 10000×g. The pellet contained phage and was reconstituted in PBS. Purified phage were put through a 0.22 μm filter if intended for mouse work.

Phage titers were determined by adding 10 μL of serially diluted phage and 200 μL of ER2738 to 3 mL of 7% agarose in LB warmed to 50° C., and poured over a warmed plate of LB agar with 20.1 g/mL tetracycline 40 μg/mL XGaI and 50 μg/mL IPTG. After overnight culture at 37° C., blue plaques were counted for calculation of pfu/μL. Plaques could be subcloned by removing an isolated plaque from the agar plate using a Pasteur pipette and extracting the phage in 100 μL of 20 mM Tris-HCl pH 8.0, 100 mM NaCl, 6 mM $MgSO_4$ at 4° C. overnight. Amplification cultures were inoculated with 20 μL of the extraction buffer, as described above.

C. Biopanning for U87R (Invasive Glioma)-specific Peptide Sequences:

Biopanning was performed as described in [61]. Subtraction cells (e.g. U87T) were released from tissue culture plastic with Puck's EDTA, and after washing with PBS, $1 \times 10^7$ cells were resuspended in 1% BSA in PBS with $1.5 \times 10^{11}$ pfu of Ph.D.-12 M13 Phage Library (New England Biolabs). The cells and phage were incubated in an eppendorf tube for 1 hour at room temperature with gentle shaking, before pelleting the cells and retaining the supernatant, which was transferred to a fresh tube with another aliquot of subtraction cells. The incubation and transfer of supernatant was performed three times, with the supernatant being transferred to an empty tube on the last round. Selection cells were released from tissue culture plastic with Puck's EDTA (e.g. U87R cells) and washed in PBS. $5 \times 10^6$ cells were resuspended in the 3× subtracted supernatant and incubated for 4 hours at 4° C. with slow shaking. The cell pellet was washed 5× in cold 1% BSA/0.1% Tween 20 in PBS five times, changing the tube after each wash. Bound phage were eluted by rocking the cells gently for 10 minutes at 4° C. in 1 mL of 0.2M Glycine-HCl pH 2.2 with 1 mg/mL BSA, and the supernatant was immediately neutralized with 150 μL of 1M Tris-HCl pH 9.1. The final library was amplified as per manufacturer's protocol.

D. Biopanning for BTIC-specific Peptide Sequences:

A BTIC-specific phage library was generated as described for the U87R library, this time using U87MG cells, U251N cells, and human normal fetal astrocytes to deplete the library of background phage, and a mixture of BTIC cell lines from different patients were used for the selection. Cells were released with EDTA if adherent, or if grown as neurospheres (e.g. BTIC cells) were separated into single cells by repeated pipetting through a small bore pipette tip. Otherwise, the subtractive and selective biopanning were performed as described for the U87R library.

E. Whole Cell ELISA:

$1 \times 10^4$ test cells were plated into a well of a 24-well dish, in 0.5 mL of media and allowed to equilibrate overnight under normal culture conditions, then the media was replaced with HEPES-buffered culture media. $5 \times 10^9$ pfu phage were added to the wells with gentle shaking for 1 hour at room temperature followed by three washes with PBS. Bound phage were detected with anti-M13-HRP antibody (GE Healthcare) and insoluble TMB substrate (Sigma).

F. Transwell Assays:

The membranes of 8 μm pore sized transwell inserts (Corning Costar) were coated with brain-like matrix (720 μL of 3 mg/mL collagen I (PureCol); 180 μL of 10×DMEM (Invitrogen); 9 μL of 1 mg/mL human plasma fibronectin (Sigma); 9 uL, of 1 mg/mL, chondroitin sulfate proteoglycans (Chemicon); 16 μL of 0.15 mg/ml, laminin (Chemicon)) on both sides, allowed to dry, then plated with $5 \times 10^4$ cells in 100 μL media in the upper chamber and 500 μL media in the lower chamber. Inclusion of collagen was essential to see the inhibitory effect of H10 (FIG. S4). $3 \times 10^{10}$ pfu of test phage were added to the upper chambers containing the cells, which were incubated for 4 hours under normal culture conditions. At the end of the incubation, the media was aspirated and the cells were fixed and stained in 1% crystal violet in 95% ethanol for one minute. Transwells were rinsed in PBS, then cells on the upper membrane surfaces were removed with a cotton swab. Cells which had migrated to the undersurface of the membranes were counted by light microscopy, and the sum of cells in five microscopic fields was recorded for each membrane.

G. Confocal Microscopy:

Adherent cells: 1.3 mm coverslips were coated with neutralized 3 mg/mL Collagen 1 (PureCol), allowed to dry, then plated with test cells at $1 \times 10^4$/mL, 0.5 mL, volume and allowed to equilibrate 20 minutes under normal culture conditions. Coverslips were fixed for 10 minutes in 3% formaldehyde in PBS, washed, then incubated in biotinylated peptide (3 mM stock) or primary antibody at a 1:100 dilution in 2% BSA/0.02% Tween 20 in PBS for 1 hour at room temperature. After washing in PBS, secondary antibody or streptavidin-Alexa 568 was applied at a dilution of 1:250 for 1 hour before coverslips were washed and mounted with DAKO mounting media with antifade.

Suspended neurospheres: 50 μL of densely suspended neurospheres were stained as described above, except in suspension in an eppendorf tube. The stained neurospheres were mounted in a drop of DAKO mounting media under a coverslip.

H. In Vivo Phage Homing:

$3 \times 10^4$ U87T or $3 \times 10^5$ U87R cells were injected in a 3 μL volume into one brain hemisphere of a SCID mouse and allowed to grow for 4 or 6 weeks respectively. For specific molecular staining, unlabeled primary antibodies, FITC-transferrin or Alexa555-cholera toxin B subunit (Invitrogen) were diluted 1:100 in 2% BSA/0.02% Tween 20 in PBS and used in place of biotinylated peptides. When needed, species-specific fluorescently labeled secondary antibodies (Molecular Probes, Invitrogen) were diluted 1:500. Primary antibodies used included anti-p75 intracellular domain pAb (Promega), anti-p75 extracellular domain mAb clone ME20.4 (Cell Signaling, Millipore), and anti-transferrin receptor (Invitrogen).

I. Sucrose/iodixanol Gradients:

Cells were scraped into 1 mL of 0.25M sucrose, 140 mM NaCl, EDTA, 20 mM Tris-HCl, pH 8.0, and dounce homogenized until cells were no longer visible by microscopy. Debris was pelleted for 5 min, 800×g and the supernatant was loaded on top of a 10 mL continuous 1.0-40% gradient, prepared by the dilution of OptiPrep (Sigma, 60% iodixanol) with 0.25M sucrose, 140 mM NaCl, 3 mM EDTA, 60 mM Tris-HCl, pH8.0. Gradients were spun in a swinging bucket rotor at 48000×g for 18 hrs and 0.5 mL fractions were collected. Total protein was precipitated from each fraction by the addition of 2 volumes of −20° C. 20 mM DTT, 15% TCA, storage at −20° C. overnight, followed by centrifugation at 4° C. for 20 minutes. Pellets were resuspended in 20 μL 1M Tris and 20 μL 2× Laemmli buffer. The entire volume was loaded into a single well for SDS-PAGE resolution and western transfer.

J. In Vivo Phage Homing:

$3\times10^4$ U87T cells, $3\times10^5$ U87R cells or $5\times10^4$ BTICs were injected in a 3 μL volume into one brain hemisphere of a SCID mouse and allowed to grow for 4, 6 or 12 weeks respectively. The mice were anaesthetized, then treated with 150 μL of 20% (w/v) mannitol for 15 minutes before injecting $5\times10^9$ pfu into the brain via the carotid. After allowing the phage to circulate for 10 minutes, unbound phage were flushed out of the circulatory system with 15 mL of PBS injected into the left ventricle after the right atrium was clipped. The brains were harvested, immediately frozen on dry ice and embedded in OCT for sectioning.

K. Immunohistochemistry:

Serial sections were fixed with cold acetone, and rehydrated through an ethanol gradient. Endogenous peroxidases in the sections were inactivated with 0.075% $H_2O_2$/methanol, and nonspecific binding was blocked with 10% normal goat serum in PBS. The sections were incubated with 1:100 diluted rabbit polyclonal anti-M13 antibody (in house), or 1:50 diluted mouse monoclonal anti-human nuclei (Chemicon) in blocking buffer. Following washing with PBS, the appropriate biotinylated secondary antibody (Vector Laboratories, http://www.vectorlabs.com) was applied. Avidin-biotin peroxidase complexes were then formed using the VECTASTAIN Elite ABC kit (Vector Laboratories) and detected by addition of SIG-MAI:AST DAB (3,39-diaminobenzidine tetrahydrochloride) (Sigma-Aldrich), which was converted to a brown reaction product by the peroxidase. Toluidine blue (for frozen sections) was used as a nuclear counterstain. Sections were then dehydrated in an ethanol/xylene series and mounted with Entellan (Electron Microscopy Sciences).

Sequence Listing

| Sequence | SEQ ID NO | Name |
|---|---|---|
| SVSVGMKPSPRP | (SEQ ID NO: 1) | (A2) |
| GISLSSYLQSTQ | (SEQ ID NO: 2) | (M32) |
| EHMALTYPFRPP | (SEQ ID NO: 3) | (C12) |
| HWAPSMYDYVSW | (SEQ ID NO: 4) | (M5) |
| RTVPDYTAHVRT | (SEQ ID NO: 5) | (M43) |
| SGHQLLLNKMPN | (SEQ ID NO: 6) | (M19) |
| TNSIWYTAPYMF | (SEQ ID NO: 7) | (H10) |
| GMSLSRQMLWSL | (SEQ ID NO: 8) | (F2) |
| HLFPQSNYGGHS | (SEQ ID NO: 9) | (M24) |
| CIQLANPPRLXG | (SEQ ID NO: 10) | (M23) |
| PSPHRQRQHILR | (SEQ ID NO: 11) | (7A) |
| QTIRIIIRRSRT | (SEQ ID NO: 12) | (10C) |
| SLHMRHKRKPRR | (SEQ ID NO: 13) | (E10) |
| SSRSMQRTLIIS | (SEQ ID NO: 14) | (3F) |
| IRSIRMRRILIL | (SEQ ID NO: 15) | (C1) |
| KTSMRPLILIHI | (SEQ ID NO: 16) | (3B) |
| TFFYGGSRGKRNNFKTEEY | (SEQ ID NO: 17) | (AngioPep-2) |
| TFFYGGSRGRRNNFRTEEY | (SEQ ID NO: 18) | AngioPep-7) |

It is claimed:

1. In a method of treating a glioblastoma muttiforme (GBM) tumor in a patient, an improvement comprising administering to the patient a composition comprising a peptide of between 12-20 amino acids in length comprising an amino acid sequence selected from the group consisting of SEQ ID NOs: 11-16 that preferentially binds to a brain tumor initiating cell (BTIC) subtype of human GBM cells characterized by their stem-cell like properties of being able to self renew, generate spheres without the addition of exogenous mitogens and growth factors, and induce tumor formation in vivo when placed in the brains of immunocompromised mice, wherein said peptide is conjugated to an anti-tumor agent capable of inhibiting the migration and invasion of said cells and/or of destroying said cells to reduce the risk of tumor recurrence in the patient.

2. The improvement of claim 1, wherein said composition is administered (i) intravenously, (ii) intra-arterially, (iii) by convection-enhanced diffusion through an intraventricutar placed catheter; (iv) by release from an intracerebral implant, (v) by physically disrupting the blood brain barrier, and/or (vi) intrathecally.

3. The improvement of claim 1, wherein said peptide is conjugated to a carrier comprising the amino acid sequence of SEQ ID NO: 17 or SEQ ID NO: 18.

4. The improvement of claim 1, wherein said composition is encapsulated within a nanoparticle.

5. The improvement of claim 1, wherein said peptide is synthesized with amino acids having the L-isomer form, the D-isomer form, or a mixture thereof.

6. The improvement of claim 1, wherein said anti-tumor agent is an alkylating agent, an anti-metabolite, a plant alkaloid or a terpenoid.

* * * * *